United States Patent
Mansiere et al.

(10) Patent No.: US 11,997,966 B2
(45) Date of Patent: Jun. 4, 2024

(54) CANOLA HYBRID VARIETY 7CN0020

(71) Applicant: BASF Agricultural Solutions Seed US LLC, Florham Park, NJ (US)

(72) Inventors: Jeffrey Mansiere, Saskatoon (CA); Stewart Brandt, Saskatoon (CA)

(73) Assignee: BASF Agricultural Solutions Seed US LLC, Florham Park, NJ (US)

( * ) Notice: Subject to any disclaimer, the term of this patent is extended or adjusted under 35 U.S.C. 154(b) by 320 days.

(21) Appl. No.: 17/237,515

(22) Filed: Apr. 22, 2021

(65) Prior Publication Data
US 2021/0329868 A1   Oct. 28, 2021

Related U.S. Application Data

(60) Provisional application No. 63/014,992, filed on Apr. 24, 2020.

(51) Int. Cl.
*A01H 6/20* (2018.01)
*A01H 5/10* (2018.01)
*A01N 57/20* (2006.01)

(52) U.S. Cl.
CPC .............. *A01H 6/202* (2018.05); *A01H 5/10* (2013.01); *A01N 57/20* (2013.01)

(58) Field of Classification Search
CPC .................................................... A01H 6/202
See application file for complete search history.

(56) References Cited

U.S. PATENT DOCUMENTS

| | | | |
|---|---|---|---|
| 4,975,374 A | 12/1990 | Goodman et al. |
| 5,426,041 A | 6/1995 | Fabijanski et al. |
| 5,478,369 A | 12/1995 | Albertsen et al. |
| 5,489,520 A | 2/1996 | Adams et al. |
| 5,550,318 A | 8/1996 | Adams et al. |
| 5,561,236 A | 10/1996 | Leemans et al. |
| 5,646,024 A | 7/1997 | Leemans et al. |
| 5,648,477 A | 7/1997 | Leemans et al. |
| 5,824,524 A | 10/1998 | Albertsen et al. |
| 5,850,014 A | 12/1998 | Albertsen et al. |
| 5,859,341 A | 1/1999 | Albertsen et al. |
| 5,874,265 A | 2/1999 | Adams et al. |
| 5,879,903 A | 3/1999 | Strauch et al. |
| 5,919,675 A | 7/1999 | Adams et al. |
| 5,969,213 A | 10/1999 | Adams et al. |
| 6,013,859 A | 1/2000 | Fabijanski et al. |
| 6,037,523 A | 3/2000 | Albertsen et al. |
| 6,063,947 A | 5/2000 | DeBonte et al. |
| 6,177,616 B1 | 1/2001 | Bartsch et al. |
| 6,222,101 B1 | 4/2001 | Patel |
| 6,265,640 B1 | 7/2001 | Albertsen et al. |
| 6,297,426 B1 | 10/2001 | Albertsen et al. |
| 6,323,392 B1 | 11/2001 | Charne |
| 6,372,965 B1 | 4/2002 | Lightner et al. |
| 9,334,483 B2 | 5/2016 | Zheng et al. |
| 9,695,434 B2 | 7/2017 | Coonrod et al. |
| 9,920,303 B2 | 3/2018 | Laga et al. |
| 2018/0352775 A1* | 12/2018 | Mansiere ................ A01H 5/10 |

FOREIGN PATENT DOCUMENTS

| | | |
|---|---|---|
| CA | 2730859 A1 | 1/2010 |
| EP | 0242246 A1 | 10/1987 |
| EP | 0333033 A1 | 9/1989 |
| WO | WO-87/05629 A1 | 9/1987 |
| WO | WO-89/10396 A1 | 11/1989 |
| WO | WO-92/03919 A1 | 3/1992 |
| WO | WO-93/11245 A1 | 6/1993 |
| WO | WO-98/56239 A1 | 12/1998 |
| WO | WO-01/79517 A2 | 10/2001 |
| WO | WO-2009/007091 A2 | 1/2009 |
| WO | WO-2016/174119 A1 | 11/2016 |

OTHER PUBLICATIONS

Daun, et al., "Use of gas liquid chromatography for monitoring the fatty acid composition of canadian rapeseed", Journal of the American Oil Chemists' Society, vol. 60, Issue 10, Oct. 1983, pp. 1751-1754.
De Greef, et al., "Evaluation of Herbicide Resistance in Transgenic Crops Under Field Conditions", Bio/Technology, vol. 7, Issue 1, Jan. 1, 1989, pp. 61-64.
Paul, et al., "The isolation and characterisation of the tapetum-specific *Arabidopsis thaliana* A9 gene", Plant Molecular Biology, vol. 19, Issue 4, Jul. 1992, pp. 611-622.
Robert W. Hartley, "Barnase and barstar: two small proteins to fold and fit together", Trends in Biochemical Sciences, vol. 14, Issue 11, Nov. 1989, pp. 450-454.

* cited by examiner

*Primary Examiner* — David H Kruse
(74) *Attorney, Agent, or Firm* — Richa Dhindsa; BASF Global Intellectual Property

(57) ABSTRACT

The invention relates to a Canola hybrid variety designated 7CN0020, essentially derived variants of that Canola hybrid variety, to the cells, seeds, plants, and plant parts of this Canola hybrid variety 7CN0020. The invention also relates to methods for producing a canola plant containing in its genetic material one or more traits introgressed into 7CN0020 through backcross conversion and/or transformation, and to the Canola seed, plant and plant part produced thereby. The invention also relates to uses of 7CN0020.

12 Claims, No Drawings

CANOLA HYBRID VARIETY 7CN0020

CROSS-REFERENCE TO RELATED APPLICATION

This application claims benefit of U.S. Provisional Patent Application No. 63/014,992 filed on Apr. 24, 2020, which is hereby incorporated by reference in its entirety.

FIELD

The present invention relates to the field of *Brassica napus* breeding (i.e. Canola breeding) and, more specifically, to the development of a new Canola hybrid variety, also referred to as "7CN0020". Canola hybrid variety 7CN0020 was deposited with the National Collection of Industrial, Food and Marine Bacteria (NCIMB) on Apr. 6, 2021 and was granted the Accession Number NCIMB 43759.

BACKGROUND

The goal of oilseed rape breeding, in particular Canola breeding is to combine various desirable traits in a single hybrid variety. The resulting hybrid variety is of high quality and possesses a relatively low level of erucic acid in the oil component and a relatively low level of glucosinolates in the meal component, so it can be termed "Canola" in accordance with the nomenclature used in plant science. Other desirable traits may include stable and high yield, resistance to pests or phytopathogenic microorganisms, tolerance to heat and drought, reducing time to crop maturity, reduction in pod shatter (shatter resistance) and pod drop, better agronomic quality, for example uniformity of plant characteristics as germination and stand establishment, growth rate, maturity, plant height, higher nutritional value, and growth rate. Canola is economically important due to the high quality vegetable oil produced from the harvested Canola seeds; therefore also an increased oil content may be of interest as a breeding goal. While breeding efforts to date have provided a number of useful Canola lines and hybrid varieties with beneficial traits, there remains a great need in the art for new Canola hybrid varieties and lines with further improved traits regarding their agronomic characteristics. Such plants would benefit farmers and consumers alike by improving overall crop yields and/or quality.

SUMMARY

In one aspect of the invention, a new Canola hybrid variety designated 7CN0020 is provided. The invention also relates to the seeds of the 7CN0020 Canola hybrid variety, wherein a representative sample of said seed has been deposited under Accession Number NCIMB 43759, to plants of the 7CN0020 Canola hybrid variety, and to methods for producing a Canola plant by crossing the 7CN0020 Canola hybrid variety with itself or another Canola plant or Canola line (whether by use of male sterility or open pollination), and to methods for producing a Canola plant containing in its genetic material one or more transgenes, and to transgenic plants produced by that method. This invention also relates to Canola seeds and plants produced by crossing the 7CN0020 Canola hybrid variety with another line. In another aspect the invention provides for a hybrid variety of Canola designated 7CN0020. The invention also provides for a plurality of seeds of the new hybrid variety, plants produced from growing the seeds of the new variety 7CN0020, and progeny of any of these. Especially, progeny retaining one or more (or all) of the "distinguishing characteristics" or one or more (or all) of the "essential morphological and physiological characteristics" or essentially all physiological and morphological characteristics of 7CN0020 referred to herein, are encompassed herein as well as methods for producing these. In one aspect, such progeny have (essentially) all the physiological and morphological characteristics of Canola hybrid variety 7CN0020 when grown under the same environmental conditions. Further, Canola seeds produced on a plant grown from these seeds is provided. In another embodiment a cell of a Canola plant is provided which is produced by crossing Canola plants and harvesting the resultant seed, wherein at least one Canola plant is Canola hybrid variety 7CN0020 wherein representative seed of said variety has been deposited under the Accession Number NCIMB 43759. In another embodiment a cell of a Canola plant is provided wherein the cell is of an F1 hybrid Canola seed, wherein a plant produced from said seed has essentially the physiological and morphological characteristics of a plant of Canola hybrid variety 7CN0020 when grown in the same environmental conditions. In another embodiment a cell of a progeny Canola variety derived from Canola hybrid variety 7CN0020 is provided, comprising a desired trait, said progeny Canola variety produced by a method comprising the steps of:

(a) crossing a Canola hybrid variety 7CN0020 plant with a plant of another Canola variety that comprises a desired trait to produce F1 progeny plants;
(b) selecting one or more F1 progeny plants that have the desired trait to produce selected progeny plants;
(c) crossing the selected progeny plants with a Canola hybrid variety 7CN0020 plant to produce backcross progeny plants;
(d) selecting for backcross progeny plants that have the desired trait and physiological and morphological characteristics of the Canola hybrid variety 7CN0020 plant to produce selected backcross progeny plants; and
(e) repeating steps (c) and (d) a sufficient number of times in succession to produce selected second or higher backcross progeny plants that comprise the desired trait and essentially all of the physiological and morphological characteristics of Canola hybrid variety 7CN0020 when grown in the same environmental conditions. In yet another embodiment of the invention, an Essentially Derived Variety of 7CN0020 having one, two or three physiological and/or morphological characteristics which are different from those of 7CN0020 and which otherwise has all the physiological and morphological characteristics of 7CN0020, wherein a representative sample of seed of variety 7CN0020 has been deposited under Accession Number NCIMB 43759 is provided. Also a plant part derived from Canola hybrid variety 7CN0020 is provided, wherein said plant part is selected from the group consisting of: harvested fruits or parts thereof, pollen, ovules, cells, leaves or parts thereof, petioles, shoots or parts thereof, stems or parts thereof, roots or parts thereof, cuttings, seeds, hypocotyl, cotyledon, flowers or parts thereof. In another aspect a method for the protection of a group of cultivated plants of Canola hybrid variety 7CN0020 in a field is provided wherein harmful microorganisms, pests or weeds are controlled by the application of a composition comprising one or more microbicidal, insecticidal or herbicidal active ingredients.

In particular embodiments, there is provided:
1. A plant cell of a Canola hybrid variety designated 7CN0020, wherein a representative sample of seed of that variety has been deposited under the Accession Number NCIMB 43759.
2. The plant cell of paragraph 1 wherein the plant cell is a seed cell.
3. The plant cell from a descendant of the Canola plant as defined in paragraph 1 limited to the first, second, third, fourth, fifth, sixth, seventh, eighth, ninth, or tenth generation.
4. The plant cell according to paragraph 3, wherein said descendant has essentially the physiological and morphological characteristics of a plant of Canola hybrid variety 7CN0020 when grown in the same environmental conditions.
5. A cell of a Canola plant produced by crossing Canola plants and harvesting the resultant seed, wherein at least one Canola plant is Canola hybrid variety 7CN0020 wherein representative seed of said variety has been deposited under the Accession Number NCIMB 43759.
6. The cell of paragraph 5, wherein the cell is of an F1 hybrid Canola seed, wherein a plant produced from said seed has essentially the physiological and morphological characteristics of a plant of Canola hybrid variety 7CN0020 when grown in the same environmental conditions.
7. A cell of a progeny Canola variety derived from Canola hybrid variety 7CN0020, comprising a desired trait, said progeny Canola variety produced by a method comprising the steps of:
(a) crossing a Canola hybrid variety 7CN0020 plant as defined in paragraph 1 or 2 with a plant of another Canola variety that comprises a desired trait to produce F1 progeny plants;
(b) selecting one or more F1 progeny plants that have the desired trait to produce selected progeny plants;
(c) crossing the selected progeny plants with a Canola hybrid variety 7CN0020 plant to produce backcross progeny plants;
(d) selecting for backcross progeny plants that have the desired trait and physiological and morphological characteristics of the Canola hybrid variety 7CN0020 plant to produce selected backcross progeny plants; and
(e) repeating steps (c) and (d) a sufficient number of times in succession to produce selected second or higher backcross progeny plants that comprise the desired trait and essentially all of the physiological and morphological characteristics of Canola hybrid variety 7CN0020 when grown in the same environmental conditions.
8. A locus converted plant cell of a locus converted plant obtained by introducing a locus conversion into Canola hybrid variety 7CN0020 wherein representative seed of said variety has been deposited under the Accession Number NCIMB 43759, and wherein the locus converted plant cell is identical to a cell from variety 7CN0020 except for the locus conversion and the locus converted plant expresses essentially the physiological and morphological characteristics of Canola hybrid variety 7CN0020.
9. The plant cell of paragraph 8, wherein the locus conversion confers a trait and the trait is: male sterility, site-specific recombination, abiotic stress tolerance, altered phosphate, altered antioxidants, altered fatty acids, altered essential amino acids, altered carbohydrates, improved shatter resistance, herbicide resistance, insect resistance or disease resistance.
10. A plant cell of an Essentially Derived Variety of 7CN0020 having one, two or three physiological and/or morphological characteristics which are different from those of 7CN0020 and which otherwise has all the physiological and morphological characteristics of 7CN0020, wherein a representative sample of seed of variety 7CN0020 has been deposited under the Accession Number NCIMB 43759.
11. Use of a Canola plant of Canola hybrid variety 7CN0020, representative seed of said variety having been deposited under the Accession Number NCIMB 43759 to breed a second plant.
12. Use of a Canola plant of Canola hybrid variety 7CN0020, representative seed of said variety having been deposited under the Accession Number NCIMB 43759 to breed an inbred.
13. The use of paragraph 12, wherein the Canola plant is used to produce a haploid that is subsequently doubled to produce a double haploid inbred.
14. Use of a Canola seed of Canola hybrid variety 7CN0020, representative seed of said variety having been deposited under the Accession Number NCIMB 43759 to produce clean seed.
15. A Canola seed cell of Canola hybrid variety 7CN0020, representative seed of said variety having been deposited under the Accession Number NCIMB 43759, wherein the seed is clean seed.
16. A Canola seed cell of Canola hybrid variety 7CN0020, representative seed of said variety having been deposited under the Accession Number NCIMB 43759, wherein the seed is treated.
17. Use of a Canola seed of Canola hybrid variety 7CN0020, representative seed of said variety having been deposited under the Accession Number NCIMB 43759 to produce treated seed.
18. The use according to paragraph 16 or 17 wherein the seed is treated with fungicide or pesticide.
19. Use of a Canola seed of Canola hybrid variety 7CN0020, representative seed of said variety having been deposited under the Accession Number NCIMB 43759 to grow subsequent generations.
20. Use of a collection of seed from a commercial bag of Canola hybrid variety 7CN0020, representative seed of said variety having been deposited under the Accession Number NCIMB 43759, to grow a commercial crop.
21. Use of a Canola hybrid plant designated 7CN0020, seed of said hybrid having been deposited under the Accession Number NCIMB 43759, to produce F2 seed.
22. Use of an F1 hybrid Canola plant designated 7CN0020, seed of said hybrid having been deposited under the Accession Number NCIMB 43759 to produce a commodity product comprising seed oil, meal, fiber or protein.
23. The use of paragraph 22, wherein the commodity product comprises seed oil.
24. Use of a Canola hybrid plant designated 7CN0020, seed of said hybrid having been deposited under the Accession Number NCIMB 43759, to produce crushed non-viable F2 seed.
25. The use of paragraph 24 wherein the crushed non-viable F2 seed is for use in the production of seed oil, meal, fibre or protein.
26. Use of a Canola seed of Canola hybrid variety 7CN0020, representative seed of said variety having been deposited under the Accession Number NCIMB 43759 as a recipient of a locus conversion.

27. Use of a Canola seed of Canola hybrid variety 7CN0020, representative seed of said variety having been deposited under the Accession Number NCIMB 43759 to grow a commercial crop.

28. A method for the protection of a group of cultivated plants of Canola hybrid variety 7CN0020 representative seed of said variety having been deposited under the Accession Number NCIMB 43759 in a field wherein weeds are controlled by the application of a composition comprising one or more herbicidal active ingredients.

29. The method according to paragraph 28 wherein one or more herbicide is selected from the group comprising amitrol, carfentrazone, clethodim, clopyralid, dicamba, diquat, ethalfluralin, ethametsulfuron-methyl, florasulam, imazamox, imazapyr, glufosinate, glufosinate-ammonium, glyphosate, MCPA amine, MCPA ester, metsulfuron, quizalofop-p-ethyl, quinclorac, saflufenacil, triallate, and trifluralin.

30. The method according to paragraph 28 or 29 wherein the herbicide is glufosinate or glufosinate ammonium.

31. The method according to paragraph 30 wherein glufosinate or glufosinate ammonium is applied in mixture or in sequence with one or more herbicides selected from the group comprising amitrol, carfentrazone, clethodim, clopyralid, dicamba, diquat, ethalfluralin, ethametsulfuron-methyl, florasulam, imazamox, imazapyr, glyphosate, MCPA amine, MCPA ester, metsulfuron, quizalofop-p-ethyl, quinclorac, saflufenacil, triallate, and trifluralin.

32. A method for the protection of a group of cultivated plants of Canola hybrid variety 7CN0020 representative seed of said variety having been deposited under the Accession Number NCIMB 43759 in a field wherein harmful microorganisms are controlled by the application of a composition comprising one or more fungicidal active ingredients.

33. The method according to paragraph 32 wherein one or more herbicide is selected from the group comprising azoxystrobin, benzovindiflupyr, boscalid, cyprodinil, fludioxonil, fluxapyroxad, fluopyram, ipfentrifluconazole, iprodione, isoflucypram, metalaxyl, mefenoxam, mefentrifluconazole, metconazole, penthiopyrad, picoxystrobin, propiconazole, prothioconazole, pyraclostrobin, pyraziflumid, pydiflumetofen, sedaxane, and tebuconazole.

34. A method for the protection of a group of cultivated plants of Canola hybrid variety 7CN0020 representative seed of said variety having been deposited under the Accession Number NCIMB 43759 in a field wherein pests are controlled by the application of a composition comprising one or more insecticidal active ingredients.

35. The method according to paragraph 34 wherein one or more insecticide is selected from the group comprising broflanilide, carbaryl, carbofuran, chlorantraniliprole, chlorpyrifos, cypermethrin, cyclaniliprole, cyhalodiamide, clothianidin, deltamethrin, dimethoate, cyantraniliprole, cyhalothrin-lambda, imidacloprid, lambda-cyhalothrin, permethrin, sulfoxaflor, spirotetramate, tetraniliprole, and thiamethoxam.

36. A method for the protection of a group of cultivated plants of Canola hybrid variety 7CN0020 representative seed of said variety having been deposited under the Accession Number NCIMB 43759 in a field wherein harmful microorganisms and/or pests are controlled by the application of a composition comprising one or more fungicidal or insecticidal active ingredients onto the seeds of said variety before seeding.

37. The method according to paragraph 36 wherein one or more fungicidal or insecticidal active ingredient is selected from the group comprising broflanilide, carbaryl, carbofuran, chlorantraniliprole, chlorpyrifos, cypermethrin, cyclaniliprole, cyhalodiamide, clothianidin, deltamethrin, dimethoate, cyantraniliprole, cyhalothrin-lambda, imidacloprid, lambda-cyhalothrin, permethrin, sulfoxaflor, spirotetramate, tetraniliprole, thiamethoxam, azoxystrobin, benzovindiflupyr, boscalid, cyprodinil, fludioxonil, fluxapyroxad, fluopyram, ipfentrifluconazole, iprodione, isoflucypram, metalaxyl, mefenoxam, mefentrifluconazole, metconazole, penthiopyrad, picoxystrobin, propiconazole, prothioconazole, pyraclostrobin, pyraziflumid, pydiflumetofen, sedaxane, and tebuconazole.

38. A plant or part thereof of a Canola hybrid variety designated 7CN0020, wherein a representative sample of seed of that variety has been deposited under the Accession Number NCIMB 43759.

39. The plant part of paragraph 38, wherein said plant part is selected from the group consisting of: harvested fruits or parts thereof, pollen, ovules, cells, leaves or parts thereof, petioles, shoots or parts thereof, stems or parts thereof, roots or parts thereof, cuttings, seeds, hypocotyl, cotyledon, and flowers or parts thereof.

40. A seed of the plant of paragraph 38.

41. A descendant plant or part thereof of the Canola plant as defined in paragraph 38 or the seed of paragraph 40 limited to the first, second, third, fourth, fifth, sixth, seventh, eighth, ninth, or tenth generation.

42. The plant part of paragraph 41, wherein said plant part is selected from the group consisting of: harvested fruits or parts thereof, pollen, ovules, cells, leaves or parts thereof, petioles, shoots or parts thereof, stems or parts thereof, roots or parts thereof, cuttings, seeds, hypocotyl, cotyledon, and flowers or parts thereof.

43. A descendant plant according to paragraph 41, wherein said descendant has essentially the physiological and morphological characteristics of a plant of Canola hybrid variety 7CN0020 when grown in the same environmental conditions.

44. A Canola plant produced by crossing Canola plants and harvesting the resultant seed, wherein at least one Canola plant is Canola hybrid variety 7CN0020 wherein representative seed of said variety has been deposited under the Accession Number NCIMB 43759.

45. The plant of paragraph 44, wherein the plant is an F1 hybrid Canola plant that has essentially the physiological and morphological characteristics of a plant of Canola hybrid variety 7CN0020 when grown in the same environmental conditions.

46. A plant of a progeny Canola variety derived from Canola hybrid variety 7CN0020, comprising a desired trait, said progeny Canola variety produced by a method comprising the steps of:
(a) crossing a Canola hybrid variety 7CN0020 plant as defined in paragraph 38 with a plant of another Canola variety that comprises a desired trait to produce F1 progeny plants;
(b) selecting one or more F1 progeny plants that have the desired trait to produce selected progeny plants;

(c) crossing the selected progeny plants with a Canola hybrid variety 7CN0020 plant to produce backcross progeny plants;

(d) selecting for backcross progeny plants that have the desired trait and physiological and morphological characteristics of the Canola hybrid variety 7CN0020 plant to produce selected backcross progeny plants; and (e) repeating steps (c) and (d) a sufficient number of times in succession to produce selected second or higher backcross progeny plants that comprise the desired trait and essentially all of the physiological and morphological characteristics of Canola hybrid variety 7CN0020 when grown in the same environmental conditions.

47. A locus converted plant obtained by introducing a locus conversion into Canola hybrid variety 7CN0020 wherein representative seed of said variety has been deposited under the Accession Number NCIMB 43759, and wherein the locus converted plant is identical to the variety 7CN0020 except for the locus conversion and the locus converted plant expresses essentially the physiological and morphological characteristics of Canola hybrid variety 7CN0020.

48. The plant of paragraph 47, wherein the locus conversion confers a trait and the trait is: male sterility, site-specific recombination, abiotic stress tolerance, altered phosphate, altered antioxidants, altered fatty acids, altered essential amino acids, altered carbohydrates, improved shatter resistance, herbicide resistance, insect resistance or disease resistance.

49. A plant of an Essentially Derived Variety of 7CN0020 having one, two or three physiological and/or morphological characteristics which are different from those of 7CN0020 and which otherwise has all the physiological and morphological characteristics of 7CN0020, wherein a representative sample of seed of variety 7CN0020 has been deposited under the Accession Number NCIMB 43759.

50. A method of producing a second plant, the method comprising selfing a Canola plant of Canola hybrid variety 7CN0020, representative seed of said variety having been deposited under the Accession Number NCIMB 43759, or breeding a Canola plant of Canola hybrid variety 7CN0020 with another plant, and growing the resulting seed.

51. A second plant, or part thereof, produced by the method of paragraph 50.

52. A seed of a second plant produced by the method of paragraph 50.

53. A method of producing an inbred plant, the method comprising selecting a plant and selfing the selected plant and its descendants for several generations to produce the inbred plant, wherein the selected plant is derived from a Canola plant of Canola hybrid variety 7CN0020, representative seed of said variety having been deposited under the Accession Number NCIMB 43759.

54. The method of paragraph 53 further comprising doubling a haploid to produce a double haploid inbred plant, wherein the haploid is the selected plant or descendant thereof derived from the Canola plant of Canola hybrid variety 7CN0020.

55. An inbred plant, or part thereof, produced by the method of paragraph 53 or 54.

56. A seed of an inbred plant produced by the method of paragraph 53 or 54.

57. A method of producing a clean seed, the method comprising the steps of obtaining a seed of Canola hybrid variety 7CN0020, representative seed of said variety having been deposited under the Accession Number NCIMB 43759, and cleaning said seed.

58. A clean seed produced by the method of paragraph 57.

59. A Canola seed of Canola hybrid variety 7CN0020, representative seed of said variety having been deposited under the Accession Number NCIMB 43759, wherein the seed is clean seed.

60. A Canola seed of Canola hybrid variety 7CN0020, representative seed of said variety having been deposited under the Accession Number NCIMB 43759, wherein the seed is treated.

61. The Canola seed according to paragraph 60, wherein the seed is treated with fungicide or pesticide.

62. A method of producing a treated seed, the method comprising the steps of obtaining a Canola seed of Canola hybrid variety 7CN0020, representative seed of said variety having been deposited under the Accession Number NCIMB 43759, and treating said seed.

63. The method of paragraph 62, wherein the treating step comprises treating with fungicide or pesticide.

64. A treated seed produced by the method of paragraph 62 or 63.

65. A method of producing a subsequent generation, the method comprising growing a Canola seed of Canola hybrid variety 7CN0020, representative seed of said variety having been deposited under the Accession Number NCIMB 43759, or a seed of a descendant thereof, to generate a plant, and selfing or breeding said plant to produce seed, and growing the seed.

66. A plant of a subsequent generation produced by the method of paragraph 65.

67. A seed of a plant of a subsequent generation produced by the method of paragraph 65.

68. A method of producing a commercial crop, the method comprising growing a collection of seed from a commercial bag of Canola hybrid variety 7CN0020, representative seed of said variety having been deposited under the Accession Number NCIMB 43759.

69. A commercial crop produced by the method of paragraph 68.

70. A method of producing F2 seed, the method comprising selfing a Canola hybrid plant designated 7CN0020, seed of said hybrid having been deposited under the Accession Number NCIMB 43759, or breeding said plant with another plant to produce F1 seed, growing said F1 seed to produce F1 plants, and selfing or breeding said F1 plants to produce F2 seed.

71. F2 seed produced by the method of paragraph 70.

72. A F2 plant grown from the F2 seed produced by the method of paragraph 70.

73. A method of producing a commodity product, the method comprising obtaining seed produced by an F1 hybrid Canola plant designated 7CN0020, seed of said hybrid having been deposited under the Accession Number NCIMB 43759, and preparing the commodity product, wherein said commodity product comprises seed oil, meal, fiber or protein.

74. The method of paragraph 73, wherein the commodity product comprises seed oil.

75. A commodity product produced by the method of paragraph 73 or 74.

76. Seed oil produced by the method of paragraph 74.

77. A method of producing crushed non-viable F2 seed, the method comprising obtaining F2 seed produced by a Canola hybrid plant designated 7CN0020, seed of said hybrid having been deposited under the Accession Number NCIMB 43759, and crushing the F2 seed.

78. Crushed non-viable F2 seed produced by the method of paragraph 77.

79. The method of paragraph 77 further comprising preparing seed oil, meal, fibre or protein from the crushed non-viable F2 seed.

80. Seed oil, meal, fibre or protein produced by the method of paragraph 79.

81. A method of producing a locus converted plant, the method comprising introducing a locus conversion into a Canola seed of Canola hybrid variety 7CN0020 wherein representative seed of said variety has been deposited under the Accession Number NCIMB 43759, and wherein the locus converted plant is identical to the variety 7CN0020 except for the locus conversion and the locus converted plant expresses essentially the physiological and morphological characteristics of Canola hybrid variety 7CN0020.

82. A locus converted plant, or a part thereof, produced by the method of paragraph 81.

83. A seed of a locus converted plant produced by the method of paragraph 81.

84. A method of producing a commercial crop, the method comprising planting Canola seed of Canola hybrid variety 7CN0020, representative seed of said variety having been deposited under the Accession Number NCIMB 43759, and growing the commercial crop.

85. A commercial crop produced by the method of paragraph 84.

86. A method of producing a progeny Canola variety derived from Canola hybrid variety 7CN0020, comprising a desired trait, said method comprising the steps of:
   (a) crossing a Canola hybrid variety 7CN0020 plant as defined in paragraph 38 with a plant of another Canola variety that comprises a desired trait to produce F1 progeny plants;
   (b) selecting one or more F1 progeny plants that have the desired trait to produce selected progeny plants;
   (c) crossing the selected progeny plants with a Canola hybrid variety 7CN0020 plant to produce backcross progeny plants;
   (d) selecting for backcross progeny plants that have the desired trait and physiological and morphological characteristics of the Canola hybrid variety 7CN0020 plant to produce selected backcross progeny plants; and
   (e) repeating steps (c) and (d) a sufficient number of times in succession to produce selected second or higher backcross progeny plants that comprise the desired trait and essentially all of the physiological and morphological characteristics of Canola hybrid variety 7CN0020 when grown in the same environmental conditions.

87. A plant of a progeny Canola variety, or part thereof, produced by the method of paragraph 86.

88. A seed of a plant of a progeny Canola variety produced by the method of paragraph 86.

89. A plant or part thereof of a Canola hybrid variety designated 7CN0020, wherein a representative sample of seed of that variety has been deposited under Accession Number NCIMB 43759, wherein the part thereof comprises at least one cell of Canola hybrid variety designated 7CN0020.

90. A method for the protection of a group of cultivated plants of the plant of paragraph 89, comprising one or more of:
   a. applying a composition comprising one or more herbicidal active ingredients, in a field wherein weeds are to be controlled;
   b. applying a composition comprising one or more fungicidal active ingredients, in a field wherein harmful microorganisms are to be controlled; and/or
   c. applying a composition comprising one or more insecticidal active ingredients, in a field wherein pests are to be controlled.

91. The method according to paragraph 90, wherein:
   a. the one or more herbicidal active ingredients is amitrol, carfentrazone, clethodim, clopyralid, dicamba, diquat, ethalfluralin, ethametsulfuron-methyl, florasulam, imazamox, imazapyr, glufosinate, glufosinate-ammonium, glyphosate, MCPA amine, MCPA ester, metsulfuron, quizalofop-p-ethyl, quinclorac, saflufenacil, triallate, and/or trifluralin;
   b. the one or more fungicidal active ingredients is azoxystrobin, benzovindiflupyr, boscalid, cyprodinil, fludioxonil, fluxapyroxad, fluopyram, ipfentrifluconazole, iprodione, isoflucypram, metalaxyl, mefenoxam, mefentrifluconazole, metconazole, penthiopyrad, picoxystrobin, propiconazole, prothioconazole, pyraclostrobin, pyraziflumid, pydiflumetofen, sedaxane, and/or tebuconazole; and/or
   c. the one or more insecticidal active ingredients is broflanilide, carbaryl, carbofuran, chlorantraniliprole, chlorpyrifos, cypermethrin, cyclaniliprole, cyhalodiamide, clothianidin, deltamethrin, dimethoate, cyantraniliprole, cyhalothrin-lambda, imidacloprid, lambda-cyhalothrin, permethrin, sulfoxaflor, spirotetramate, tetraniliprole, and/or thiamethoxam.

92. The method according to paragraph 91, wherein the one or more herbicidal active ingredients comprises glufosinate or glufosinate ammonium.

93. A method of producing an inbred plant, the method comprising selecting a plant and selfing the selected plant and its descendants for several generations to produce the inbred plant, wherein the selected plant is derived from the plant of paragraph 89.

94. The method of paragraph 93, further comprising doubling a haploid to produce a double haploid inbred plant, wherein the haploid is the selected plant or descendant thereof derived from the Canola plant of Canola hybrid variety 7CN0020.

95. A method of producing F2 seed, the method comprising selfing the Canola hybrid plant of paragraph 89, or breeding said plant with another plant to produce F1 seed, growing said F1 seed to produce F1 plants, and selfing or breeding said F1 plants to produce F2 seed.

96. A method of producing a clean seed, the method comprising obtaining the seed of Canola hybrid variety 7CN0020, wherein a representative sample of seed of that variety has been deposited under Accession Number NCIMB 43759, and cleaning said seed.

97. A treated seed of Canola hybrid variety 7CN0020, representative seed of said variety having been deposited under the Accession Number NCIMB 43759.

98. A method of producing a treated seed of paragraph 97, the method comprising obtaining the seed of Canola hybrid variety 7CN0020, wherein a representative sample of seed of that variety has been deposited under Accession Number NCIMB 43759, and treating said seed.

99. A method of producing a commodity product, the method comprising obtaining seed produced by an F1 hybrid Canola plant designated 7CN0020, seed of said hybrid having been deposited under Accession Number NCIMB 43759, and preparing the commodity product, wherein said commodity product comprises seed oil, meal, fiber, or protein.

100. A method of producing a commercial crop, the method comprising planting the seed of Canola hybrid variety 7CN0020, wherein a representative sample of seed of that variety has been deposited under Accession Number NCIMB 43759, and growing the commercial crop.

Definitions

In the description and tables which follow, a number of terms are used. In order to aid in a clear and consistent understanding of the specification, the following definitions and evaluation criteria are provided.

"Canola" refers herein to seeds or plants of the genus Brassica (*Brassica napus, Brassica rapa* or *Brassica juncea*) from which the oil shall contain less than 2% erucic acid in its fatty acid profile and the solid component shall contain less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil-free solid.

The terms "Canola hybrid variety 7CN0020", "7CN0020", or "Canola hybrid variety designated 7CN0020", "Canola variety 7CN0020" are used interchangeably herein and refer to a plant of Canola hybrid variety 7CN0020, representative seed of which having been deposited under Accession Number NCIMB 43759. As used herein, the term "plant" includes the whole plant or any parts such as plant organs, plant cells, plant protoplasts, plant cell cultures or tissue cultures from which whole plants can be regenerated, plant callus, plant cell clumps, plant transplants, seedlings, plant cells that are intact in plants, plant clones or micropropagations, or parts of plants (e.g., harvested tissues, fruits or organs), such as plant cuttings, vegetative propagations, embryos, pollen, ovules, flowers, leaves, fruits, fruit flesh, seeds, clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves.

"Tissue culture" refers to a composition comprising isolated cells of the same or a different type or a collection of such cells organized into parts of a plant. Tissue culture of various tissues of Canola and regeneration of plants therefrom is well known and widely published (see, e.g., Sang-Gu et al. (1988), Plant Cell, Tissue and Organ Culture 12: 67-74; Colijn-Hooymans (1994), Plant Cell, Tissue and Organ Culture 39: 211-217). Similarly, the skilled person is well-aware how to prepare a "cell culture".

A plant having "(essentially) all the physiological and morphological characteristics" means a plant having the physiological and morphological characteristics when grown under the same environmental conditions of the plant from which it was derived, e.g. the progenitor plant, the parent, the recurrent parent, the plant used for tissue- or cell culture, etc. In certain embodiments the plant has all the physiological and morphological characteristics, except for certain characteristics mentioned, e.g. the characteristic(s) derived from a converted or introduced gene or trait and/or except for the characteristics which differ in an EDV.

A plant having one or more "essential physiological and/or morphological characteristics" or one or more "distinguishing characteristics" refers to a plant having (or retaining) one or more of the characteristics mentioned in Table 1 when grown under the same environmental conditions that distinguish 7CN0020 from the most similar varieties, such as but not limited to oil content, protein content, yield, time to maturity, disease resistance, standability, lodging or shatter resistance. The physiological and/or morphological characteristics mentioned above are commonly evaluated at significance levels of 1%, 5% or 10% significance level, when measured under the same environmental conditions. For example, a progeny plant of Canola hybrid variety 7CN0020 may have one or more (or all) of the essential physiological and/or morphological characteristics of Canola hybrid variety 7CN0020 listed in Table 1, as determined at the 5% significance level when grown under the same environmental conditions. As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties. "Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Selfing" refers to self-pollination of a plant, i.e., the transfer of pollen from the anther to the stigma of the same plant.

"Crossing" refers to the mating of two parent plants.

"Average" refers herein to the arithmetic mean. "Substantially equivalent" refers to a characteristic that, when compared, does not show a statistically significant difference (e.g., p=0.05) from the mean.

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one Canola line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant of a Canola hybrid variety 7CN0020. Progeny may be derived by regeneration of cell culture or tissue culture or parts of a plant of Canola hybrid variety 7CN0020 or selfing of a plant designated 7CN0020 or by producing seeds of a plant of Canola hybrid variety 7CN0020. In further embodiments, progeny may also encompass plants derived from crossing of at least one plant of Canola hybrid variety 7CN0020 with another Canola plant of the same or another variety or (breeding) line, or wild plants of *Brassica* species, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to Canola plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a Canola variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a Canola plant by transformation. A plant comprising a transgene stably integrated into its genome is referred to as "transgenic plant".

The term "mean" refers to the arithmetic mean of several measurements. The skilled person understands that the appearance of a plant depends to some extent on the growing conditions of said plant. Thus, the skilled person will know typical growing conditions for Canola plants described herein. The mean, if not indicated otherwise within this application, refers to the arithmetic mean of measurements on at least different, randomly selected plants of a variety or line.

The term "Anther Fertility" means the ability of a plant to produce pollen; measured by pollen production. 1=sterile, 9=all anthers shedding pollen (vs. Pollen Formation which is amount of pollen produced).

The term "Anther Arrangement" means the general disposition of the anthers in typical fully opened flowers is observed.

The term "Chlorophyll Content" means the typical chlorophyll content of the mature seeds is determined by using methods recommended by the Western Canada Canola/Rapeseed Recommending Committee (WCC/RRC). 1=low (less than 8 ppm), 2=medium (8 to ppm), 3=high (greater than 15 ppm). Also, chlorophyll could be analyzed using NIR (Near Infrared) spectroscopy as long as the instrument is calibrated according to the manufacturer's specifications.

The term "CMS" means the abbreviation for cytoplasmic male sterility.

The term "Cotyledon" means the cotyledon being a part of the embryo within the seed of a plant; it is also referred to as a seed leaf. Upon germination, the cotyledon may become the embryonic first leaf of a seedling.

The term "Cotyledon Length" means the distance between the indentation at the top of the cotyledon and the point where the width of the petiole is approximately 4 mm.

The term "Cotyledon Width" means the width at the widest point of the cotyledon when the plant is at the two to three-leaf stage of development. 3=narrow, 5=medium, 7=wide. The term "CV %" means the abbreviation for coefficient of variation.

The term "Disease Resistance" means the resistance to various diseases is evaluated and is expressed on a scale of 0=not tested, 1=resistant, 3=moderately resistant, 5=moderately susceptible, 7=susceptible, and 9=highly susceptible.

The term "Erucic Acid Content" means the percentage of the fatty acids in the form of C22:1 as determined by one of the methods recommended by the WCC/RRC, being AOCS Official Method Ce 2-66 Preparation of Methyl esters of Long-Chain Fatty Acids or AOCS Official Method Ce 1-66 Fatty Acid Composition by Gas Chromatography.

The term "Fatty Acid Content" means the typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of Daun, et al., (1983) *J. Amer. Oil Chem. Soc.* 60:1751 to 1754.

The term "Flower Bud Location" describes the determination to be made whether typical buds are disposed above or below the most recently opened flowers.

The term "Flower Date 50%" (Same as Time to Flowering) describes the number of days from planting until 50% of the plants in a planted area have at least one open flower.

The term "Flower Petal Coloration" means the coloration of open exposed petals on the first day of flowering is observed.

The term "Frost Tolerance (Spring Type Only)" means the ability of young plants to withstand late spring frosts at a typical growing area is evaluated and is expressed on a scale of 1 (poor) to 5 (excellent).

The term "Gene Silencing" means the interruption or suppression of the expression of a gene at the level of transcription or translation. The term "Genotype" refers to the genetic constitution of a cell or organism.

The term "Glucosinolate Content" means the total glucosinolates of seed at 8.5% moisture, as measured by AOCS Official Method AK-1-92 (determination of glucosinolates content in rapeseed-colza by HPLC), is expressed as micromoles per gram of defatted, oil-free meal. Capillary gas chromatography of the trimethylsilyl derivatives of extracted and purified desulfoglucosinolates with optimization to obtain optimum indole glucosinolate detection is described in *"Procedures of the Western Canada Canola/Rapeseed Recommending Committee Incorporated for the Evaluation and Recommendation for Registration of Canola/Rapeseed Candidate Cultivars in Western Canada"*. Also, glucosinolates could be analyzed using NIR (Near Infrared) spectroscopy as long as the instrument is calibrated according to the manufacturer's specifications.

The term "Grain" means the seed produced by the plant or a self or sib of the plant that is intended for food or feed use.

The term "Green Seed" means the number of seeds that are distinctly green throughout as defined by the Canadian Grain Commission expressed as a percentage of seeds tested.

The term "Herbicide Resistance" means the resistance to various herbicides when applied at standard recommended application rates is expressed on a scale of 1 (resistant), 2 (tolerant), or 3 (susceptible).

The term "Leaf Anthocyanin Coloration" means the presence or absence of leaf anthocyanin coloration, and the degree thereof if present, are observed when the plant has reached the 9- to 11-leaf stage.

The term "Leaf Attachment to Stem" means the presence or absence of clasping where the leaf attaches to the stem, and when present the degree thereof, are observed.

The term "Leaf Attitude" means the disposition of typical leaves with respect to the petiole is observed when at least 6 leaves of the plant are formed.

The term "Leaf Color" means the leaf blade coloration is observed when at least six leaves of the plant are completely developed.

The term "Leaf Glaucosity" means the presence or absence of a fine whitish powdery coating on the surface of the leaves, and the degree thereof when present, are observed. The term "Leaf Length" means the length of the leaf blades and petioles are observed when at least six leaves of the plant are completely developed.

The term "Leaf Lobes" means the fully developed upper stem leaves are observed for the presence or absence of leaf lobes when at least 6 leaves of the plant are completely developed.

The term "Leaf Margin Indentation" means the rating of the depth of the indentations along the upper third of the margin of the largest leaf. 1=absent or very weak (very shallow), 3=weak (shallow), 5=medium, 7=strong (deep), 9=very strong (very deep).

The term "Leaf Margin Hairiness" means the leaf margins of the first leaf are observed for the presence or absence of pubescence, and the degree thereof, when the plant is at the two leaf-stage.

The term "Leaf Margin Shape" means the visual rating of the indentations along the upper third of the margin of the largest leaf. 1=undulating, 2=rounded, 3=sharp. The term "Leaf Surface" means the leaf surface is observed for the presence or absence of wrinkles when at least six leaves of the plant are completely developed.

The term "Leaf Tip Reflexion" means the presence or absence of bending of typical leaf tips and the degree thereof, if present, are observed at the six to eleven leaf-stage.

The term "Leaf Upper Side Hairiness" means the upper surfaces of the leaves are observed for the presence or absence of hairiness, and the degree thereof if present, when at least six leaves of the plant are formed.

The term "Leaf Width" means the width of the leaf blades is observed when at least six leaves of the plant are completely developed.

The term "Locus" means a specific location on a chromosome.

The term "Locus Conversion" means a locus conversion refers to plants within a variety that have been modified in a manner that retains the overall genetics of the variety and further comprises one or more loci with a specific desired trait, such as male sterility, insect, disease or herbicide resistance. Examples of single locus conversions include mutant genes, transgenes and native traits finely mapped to a single locus. One or more locus conversion traits may be introduced into a single Canola variety.

The term "Lodging Resistance" means the resistance to lodging at maturity is observed. 1=not tested, 3=poor, 5=fair, 7=good, 9=excellent.

The term "LSD" is the abbreviation for least significant difference.

The term "Maturity" means the number of days from planting to maturity is observed, with maturity being defined as the plant stage when pods with seed change color, occurring from green to brown or black, on the bottom third of the pod-bearing area of the main stem.

The term "NMS" is the abbreviation for nuclear male sterility.

The term "Number of Leaf Lobes" means the frequency of leaf lobes, when present, is observed when at least six leaves of the plant are completely developed.

The term "Oil Content" means the typical percentage by weight oil present in the mature whole dried seeds is determined by ISO 10565:1993 Oilseeds Simultaneous determination of oil and water—Pulsed NMR method. Also, oil could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance.

The term "Pedicel Length" means the typical length of the silique stem when mature is observed. 3=short, 5=medium, 7=long.

The term "Petal Length" means the lengths of typical petals of fully opened flowers are observed. 3=short, 5=medium, 7=long. The term "Petal Width" means the widths of typical petals of fully opened flowers are observed. 3=short, 5=medium, 7=long.

The term "Petiole Length" means the length of the petioles is observed, in a line forming lobed leaves, when at least six leaves of the plant are completely developed. 3=short, 5=medium, 7=long.

The term "Plant Height" means the overall plant height at the end of flowering is observed. 3=short, 5=medium, 7=tall.

The term "Ploidy" refers to the number of chromosomes exhibited by the line, for example diploid or tetraploid.

The term "Pod Anthocyanin Coloration" means the presence or absence at maturity of silique anthocyanin coloration, and the degree thereof if present, are observed.

The term "Pod (Silique) Beak Length" means the typical length of the silique beak when mature is observed. 3=short, 5=medium, 7=long. The term "Pod Habit" means the typical manner in which the siliques are borne on the plant at maturity is observed.

The term "Pod (Silique) Length" means the typical silique length observed. 1=short (less than 7 cm), 5=medium (7 to 10 cm), 9=long (greater than 10 cm).

The term "Pod (Silique) Attitude" means a visual rating of the angle joining the pedicel to the pod at maturity. 1=erect, 3=semi-erect, 5=horizontal, 7=semi-drooping, 9=drooping.

The term "Pod Type" means the overall configuration of the silique observed.

The term "Pod (Silique) Width" means the typical pod width observed when mature. 3=narrow (3 mm), 5=medium (4 mm), 7=wide (5 mm).

The term "Pollen Formation" means the relative level of pollen formation observed at the time of dehiscence.

The term "Protein Content" means the typical percentage by weight of protein in the oil free meal of the mature whole dried seeds when determined by AOCS Official Method Ba4e-93 Combustion Method for the Determination of Crude Protein. Also, protein could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance.

The term "Resistance" means the ability of a plant to withstand exposure to an insect, disease, herbicide, or other condition. A resistant plant variety or hybrid will have a level of resistance higher than a comparable wild-type variety or hybrid.

"Tolerance" is a term commonly used in crops affected by abiotic stress, diseases or pests and is used to describe an improved level of field resistance.

The term "Root Anthocyanin Coloration" means the presence or absence of anthocyanin coloration in the skin at the top of the root, observed when the plant has reached at least the six-leaf stage.

The term "Root Anthocyanin Expression" means that when anthocyanin coloration is present in skin at the top of the root, it further is observed for the exhibition of a reddish or bluish cast within such coloration when the plant has reached at least the six-leaf stage.

The term "Root Anthocyanin Streaking" means when anthocyanin coloration is present in the skin at the top of the root, it further is observed for the presence or absence of streaking within such coloration when the plant has reached at least the six-leaf stage.

The term "Root Chlorophyll Coloration" means the presence or absence of chlorophyll coloration in the skin at the top of the root is observed when the plant has reached at least the six-leaf stage.

The term "Root Coloration Below Ground" means the coloration of the root skin below ground observed when the plant has reached at least the six-leaf stage. Root Depth in Soil" means the typical root depth is observed when the plant has reached at least the six-leaf stage.

The term "Root Flesh Coloration" means the internal coloration of the root flesh observed when the plant has reached at least the six-leaf stage. The term "SE" means the abbreviation for standard error.

The term "Seedling Growth Habit" means the growth habit of young seedlings is observed for the presence of a weak or strong rosette character. 1=weak rosette, 9=strong rosette.

The term "Seeds Per Pod" means the average number of seeds per pod is observed.

The term "Seed Coat Color" means the seed coat color of typical mature seeds is observed. 1=black, 2=brown, 3=tan, 4=yellow, 5=mixed, 6=other.

The term "Seed Coat Mucilage" means the presence or absence of mucilage on the seed coat is determined and is expressed on a scale of 1 (absent) to 9 (present). During such determination a petri dish is filled to a depth of 0.3 cm. with water provided at room temperature. Seeds are added to the petri dish and are immersed in water where they are allowed to stand for five minutes. The contents of the petri dish containing the immersed seeds are then examined under a stereo microscope equipped with transmitted light. The presence of mucilage and the level thereof is observed as the intensity of a halo surrounding each seed.

The term "Seed Size" means the weight in grams of 1,000 typical seeds is determined at maturity while such seeds exhibit a moisture content of approximately 5 to 6 percent by weight.

The term "Shatter Resistance" means the resistance to silique shattering is observed at seed maturity. 1=not tested, 3=poor, 5=fair, 7=good, 9=does not shatter.

The term "SI" is the abbreviation for self-incompatible.

The term "Speed of Root Formation means the typical speed of root formation observed when the plant has reached the four to eleven-leaf stage.

The term "SSFS" is the abbreviation for *Sclerotinia sclerotiorum* Field Severity score, a rating based on both percentage infection and disease severity.

The term "Stem Anthocyanin Intensity" means the presence or absence of leaf anthocyanin coloration and the intensity thereof, if present, are observed when the plant has reached the nine to eleven-leaf stage. 1=absent or very weak, 3=weak, 5=medium, 7=strong, 9=very strong.

The term "Stem Lodging" at Maturity means a visual rating of a plant's ability to resist stem lodging at maturity. 1=very weak (lodged}, 9=very strong (erect).

The term "Time to Flowering" means the determination of the number of days when at least 50 percent of the plants have one or more open buds on a terminal raceme in the year of sowing.

The term "Seasonal Type" means whether the new line is considered to be primarily a Spring or Winter type of Canola.

The term "Winter Survival (Winter Type Only)" means the ability to withstand winter temperatures at a typical growing area is evaluated and is expressed on a scale of 1 (poor) to 5 (excellent).

DETAILED DESCRIPTION

Breeding of new varieties, lines and hybrids is achieved by using techniques of mutagenesis, crossing and selection on a set of parental lines taking advantage of the plant's method of pollination (self-, sib- or cross-pollination). Within such a breeding program the breeder performs multiple rounds of mutagenesis, crossing and selection without having necessarily control of the results on a cellular or molecular level. After each round the breeder will select the germplasm for the next round. Environmental factors like climate, soil and location will influence in addition to the unique genetic basis of each parent line of every round to the results of the breeding process. Consequently the molecular, physiological and anatomical characteristics of the resulting new varieties, lines or hybrids cannot be predicted due to the huge amount of possible genetic combinations. Consequently high efforts in breeding are needed a develop new and superior Canola varieties Common techniques in Canola breeding programs includes but is not limited to techniques such as mass selection, backcrossing, pedigree breeding and haploidy (see Downey and Rakow, (1987) "Rapeseed and Mustard" In: Principles of Cultivar Development, Fehr, (ed.), pp 437-486; New York; Macmillan and Co.; Thompson, (1983) "Breeding winter oilseed rape Brassica napus"; Advances in Applied Biology 7:1-104; and Ward, et. al., (1985) Oilseed Rape, Farming Press Ltd., Wharfedale Road, Ipswich, Suffolk). By selecting recurrently populations of either self- or crosspollinating Canola parent varieties based on their superior characteristics the Canola plants are improved and are then further used for intercrossing to produce a new population to ensure that quantitatively inherited traits controlled by numerous genes are improved. For a simply inherited, highly heritable trait backcross breeding (ie recurrent crossing of the same parent after the first transfer crossing) can be used to transfer genes from the donor patent into another line that serves as the recurrent parent. This approach has been used for breeding disease resistant phenotypes of many plant species, and has been used to transfer low erucic acid and low glucosinolate content into lines and breeding populations of Canola. Pedigree breeding and recurrent selection breeding methods are used to develop varieties from breeding populations. Pedigree breeding starts with the crossing of two genotypes, each of which may have one or more desirable characteristics that is lacking in the other or which complements the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self pollination and selection. Typically in the pedigree method of breeding, five or more generations of selfing and selection are practiced: F1 to F2; F2 to F3; F3 to F4; F4 to F5, etc. For example, two parents that are believed to possess favorable complementary traits are crossed to produce an F1. An F2 population is produced by selfing one or several F1's or by intercrossing two F1's (i.e., sib mating). Selection of the best individuals may begin in the F2 population, and beginning in the F3 the best individuals in the best families are selected. Replicated testing of families can begin in the F4 generation to improve the effectiveness of selection for traits with low heritability. At an advanced stage of inbreeding (i.e., F5 and F1), the best lines or mixtures of phenotypically similar lines commonly are tested for potential release as new cultivars. Backcrossing may be used in conjunction with pedigree breeding; for example, a combination of backcrossing and pedigree breeding with recurrent selection has been used to incorporate blackleg resistance into certain cultivars of Brassica napus. Plants that have been self-pollinated and selected for type for many generations become homozygous at almost all gene loci and produce a uniform population of true breeding progeny. If desired, double-haploid methods can also be used to extract homogeneous lines. A cross between two different homozygous lines produces a uniform population of hybrid plants that may be heterozygous for many gene loci. A cross of two plants each heterozygous at a number of gene loci will produce a population of hybrid plants that differ genetically and will not be uniform. The choice of breeding or selection methods depends on the mode of plant reproduction, the heritability of the trait(s) being improved, and the type of cultivar used commercially, such as F1 hybrid variety or open pollinated variety. A true breeding homozygous line can also be used as a parental line (inbred line) in a commercial hybrid. If the line is being developed as an inbred for use in a hybrid, an appropriate pollination control system should be incorporated in the line. Suitability of an inbred line in a hybrid combination will depend upon the combining ability (general combining ability or specific combining ability) of the inbred. Various breeding procedures are also utilized with these breeding and selection methods. The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed. In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique. The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed. If desired, doubled-haploid methods can be used to extract homogeneous lines. Molecular markers, including techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (APPCR), DNA Amplification Fingerprinting (OAF), Sequence Characterized Amplified 10 Regions (SCARs), Amplified Fragment Length Polymorphisms (AFLPs), Simple Sequence Repeats (SSRs) and Single Nucleotide Polymorphisms (SNPs), may be used in plant breeding methods. One use of molecular markers is Quantitative Trait Loci (QTL) mapping. QTL mapping is the use of markers which are known to be closely linked to alleles that have measurable effects on a quantitative trait.

Selection in the breeding process is based upon the accumulation of markers linked to the positive effecting alleles and/or the elimination of the markers linked to the negative effecting alleles in the plant's genome. Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection or Marker Assisted Selection (MAS). The production of doubled haploids can also be used for the development of inbreds in the breeding program. In *Brassica napus*, microspore culture technique is used in producing haploid embryos. The haploid embryos are then regenerated on appropriate media as haploid plantlets, doubling chromosomes of which results in doubled haploid plants. This can be advantageous because the process omits the generations of selfing needed to obtain a homozygous plant from a heterozygous source.

The development of a canola hybrid in a canola plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in canola, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Controlling Self-Pollination

Canola varieties are mainly self-pollinated; therefore, self-pollination of the parental varieties must be controlled to make hybrid development feasible. In developing improved new *Brassica* hybrid varieties, breeders may use self-incompatible (SI), cytoplasmic male sterile (CMS) or nuclear male sterile (NMS) *Brassica* plants as the female parent. In using these plants, breeders are attempting to improve the efficiency of seed production and the quality of the F1 hybrids and to reduce the breeding costs. When hybridization is conducted without using SI, CMS or NMS plants, it is more difficult to obtain and isolate the desired traits in the progeny (F1 generation) because the parents are capable of undergoing both crosspollination and self-pollination. If one of the parents is a SI, CMS or NMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross. In one instance, production of F1 hybrids includes crossing a NMS *Brassica* female parent with a pollen-producing male *Brassica* parent. To reproduce effectively, however, the male parent of the F1 hybrid must have a fertility restorer gene (Rf gene). The presence of an Rf gene means that the F1 generation will not be completely or partially sterile, so that either self-pollination or cross pollination may occur. Self-pollination of the F1 generation to produce several subsequent generations is important to ensure that a desired trait is heritable and stable and that a new variety has been isolated. One approach to ensure cross-pollination is the male sterility system established in the Seedlink™ technology (WO-A 89/10396).

Seedlink™ uses the transgenic expression of three different proteins in the respective plant. The first protein Barnase is an extracellular ribonuclease isolated from *Bacillus amyloliquefaciens*. The enzyme is inhibited by its corresponding intracellular inhibitor barstar (Hartley, Trends in Biochemical Sciences 1989, 14(11), 450). The DNA which codes for Barnase has been introduced into *Brassica* using *Agrobacterium* transformation technology under the control of a tapetum specific promoter and thereby leads to the suppression of the production of fertile male gametes. *Agrobacterium* transformation is described in CA-A 1 341 419. Together with Barnase gene being therefore a male sterility gene also a gene coding for a phosphinothricin-N-acetyl-transferase (PAT) enzyme isolated from *Streptomyces hygroscopicus* has been introduced into *Brassica* using *Agrobacterium* transformation resulting in a male sterile female line resulting from the Ms8 event. Transgenic plants expressing the PAT gene are described in WO-A 87/05629. The expression of the PAT gene in a plant provides the plant with the ability to detoxify the herbicide Glufosinate. Glufosinate or its ammonium salt DL phosphinothricin is a broad spectrum herbicide and desiccant as it inhibits glutamine synthetase thereby leading to toxic ammonium accumulation in the plant. Plants which have been transformed with the PAT gene are able to acetylate the herbicide and thereby detoxify it into an inactive compound. Therefore these plants are resistant to Glufosinate.

In order to restore fertility for producing the hybrid F1 population the fertility restorer line was produced by the introduction of the barstar gene also under the control of a tapetum specific promoter together with the PAT gene using *Agrobacterium* transformation as described in WO-A 87/05629. The presence of the PAT gene in the transformants both for the male sterile and restorer lines can therefore serve as a marker for the successful transformation and provides the herbicide resistance. Restorer lines typically comprise the RF3 event. In order to produce the F1 hybrid generation the female line being male sterile comprising the Ms8 event is crossed with the male fertile restorer line comprising the RF3 event resulting in a F1 population carrying MS8/RF3.

Shatter Resistance

Reducing the shattering of the pods in Brassicaceae is desirable trait as high pod shatter resistance reduces yield losses during harvest or high winds due the unwanted shattering of pods. Pod shatter resistance might be found in varying levels within Brassicaceae. Several relevant genes important in controlling shatter resistance have been identified, eg SHATTERPROOF1 and SHATTERPROOF2 (Liljegren et al., 2000, Nature 404, 766-770), the INDEHISCENT gene IND1 (Liljegren et al., 2004, Cell 116: 843-853; PCT publication WO 01/79517) or the ALCATRAZ gene ALC1 (Rajani et al. 2001, Current Biology 11, 1914-1922). Mutant alleles of these genes may be used to modify and improve shatter resistance in Brassicaceae, in particular in Canola hybrids as described in CA-A 2,730,859.

Disease Resistance

Several diseases of Brassicaceae, in particular *Brassica napus* and hybrids thereof, are of high importance and are also addressed by breeding approaches.

Blackleg, also known as stem cancer, is caused by *Leptosphaeria maculans*. The fungus infects the plants late in the season and may cause significant yield losses. The fungus overwinters in infected plant debris in the field and then infects lower stem and upper root parts leading to wide spread infections in susceptible *Brassica* plants. Blackleg is managed to a large extent through genetic resistance; however constant efforts in breeding in order to face the challenges by new races of the fungus overcoming established resistance.

Clubroot, caused by the protist *Plasmodiophora brassicae*, has become a significant thread to Brassicaceae, in particular in Western Canada. The pathogen causes swellings on the root which ultimately leads to premature death of the plant. Due to long survival time—up to 20 years—of resting spores in the soil, a field infected with *Plasmodiophora brassicae* will be impacted for a long time. In addition, movement of infected soil, e.g. through farm equipment, often will lead to further spreading of the infection. Until now, options to control *Plasmodiophora brassicae* by agrochemicals are practically non-existent, and the disease is mainly managed through extended crop rotation as well as sanitation practices or restricting access to the field. Thus for clubroot, genetic resistance could be key in managing the disease; however, knowledge on clubroot races and associated resistance genes is limited. Breeding for clubroot resistance is therefore an essential task and objective in Brassicaceae breeding.

Hybrid Development

7CN0020 is a fully restored spring *Brassica napus* hybrid with a glufosinate resistance gene, based on SeedLink hybridization system as described above. It was developed at the Breeding Centre of BASF Canada Inc. in Saskatoon, Canada. It is a single cross hybrid produced by crossing a female parent expressing the PAT and the barnase gene under the control of a tapetum specific promoter by a restorer—male R line expressing the PAT and the barstar gene under the control of a tapetum specific promoter. A pollination control system and effective transfer of pollen from one parent to the other offers improved plant breeding and an effective method for producing hybrid canola seed and plants. For example, the Seedlink (NMS) system, developed using *Agrobacterium* transformation, is one of the most frequently used methods of hybrid production. It provides stable expression of the male sterility trait and an effective restorer gene.

For most traits the true genotypic value may be masked by other confounding plant traits or environmental factors. One method for identifying a superior plant is to observe its performance relative to other experimental plants and to one or more widely grown standard varieties. If a single observation is inconclusive, replicated observations provide a better estimate of the genetic worth. Proper testing should detect any major faults and establish the level of superiority or improvement over current varieties. In addition to showing superior performance, there must be a demand for a new variety that is compatible with industry standards or which creates a new market. The introduction of a new variety commonly will incur additional costs to the seed producer, the grower, the processor and the consumer, for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically. These processes, which lead to the final step of marketing and distribution, usually take from approximately six to twelve years from the time the first cross is made. Therefore, the development of new varieties is a time-consuming process that requires precise forward planning, efficient use of resources, and a minimum of changes in direction. Further, as a result of the advances in sterility systems, lines are developed that can be used as an open pollinated variety (i.e., a pureline cultivar sold to the grower for planting) and/or as a sterile inbred (female) used in the production of F1 hybrid seed. In the latter case, favorable combining ability with a restorer (male) would be desirable. The resulting hybrid seed would then be sold to the grower for planting. Combining ability of a line, as well as the performance of the line per se, is a factor in the selection of improved canola lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines. Hybrid seed production requires inactivation of pollen produced by the female parent. Incomplete inactivation of the pollen provides the potential for self-pollination. This inadvertently self-pollinated seed may be unintentionally harvested and packaged with hybrid seed. Similarly, because the male parent is grown next to the female parent in the field, there is also the potential that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in hybrid seed bags exists, the occurrence is rare because much care is taken to avoid such inclusions. These self-pollinated plants can be identified and selected by one skilled in the art, through either visual or molecular methods. *Brassica napus* canola plants, absent the use of sterility systems, are recognized to commonly be self-fertile with approximately 70 to 90 percent of the seed normally forming as the result of self-pollination. The percentage of cross pollination may be further enhanced when populations of recognized insect pollinators at a given growing site are greater. Thus open pollination is often used in commercial canola production. Since canola variety 7CN0020 is a hybrid produced from substantially homogeneous parents, it can be reproduced by planting seeds of such parents, growing the resulting canola plants under controlled pollination conditions with adequate isolation so that cross-pollination occurs between the parents, and harvesting the resulting hybrid seed using conventional agronomic practices. Locus Conversions of Canola Variety 7CN0020 represents a new base genetic line into which a new locus or trait may be introduced. Direct transformation and backcrossing represent two important methods that can be used to accomplish such an introgression. The term locus conversion is used to designate the product of such an introgression. To select and develop a superior hybrid, it is necessary to identify and select genetically unique individuals that occur in a segregating population. The segregating population is the result of a combination of crossover events plus the independent assortment of specific combinations of alleles at many gene loci that results in specific and unique genotypes. Once such a variety is developed its value to society is substantial since it is important to advance the germplasm base as a whole in order to maintain or improve traits such as yield, disease resistance, pest resistance and plant performance in extreme weather conditions. Locus conversions are routinely used to add or modify one or a few traits of such a line and this further enhances its value and usefulness to society. Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent. Traits may be used by those of ordinary skill in the art to characterize progeny. In one aspect a locus converted plant cell of a locus converted plant is described which is obtained by introducing a locus conversion into Canola hybrid variety 7CN0020, and wherein the locus converted plant cell is identical to a cell from variety 7CN0020 except for the locus conversion and the locus converted plant expresses essentially the physiological and morphological characteristics of Canola hybrid variety 7CN0020. In another aspect the locus conversion confers a trait and the trait is selected from the group comprising male sterility, site-specific recombination, abiotic stress resistance, altered phosphate, altered antioxidants, altered fatty acids, altered essential amino acids, altered carbohydrates, improved shatter resistance, improved lodging, herbicide resistance, insect resistance or disease resistance.

Traits are commonly evaluated at a significance level, such as a 1%, 5% or 10% significance level, when measured in plants grown in the same environmental conditions. For example, a locus conversion of 7CN0020 may be characterized as having essentially the same phenotypic traits as 7CN0020. Molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. A locus conversion of 7CN0020 will retain the genetic integrity of 7CN0020. A locus conversion of 7CN0020 will comprise at least 92%, 93%, 94%, 95%, 96%, 97%, 98% or 20 99% of the base genetics of 7CN0020. For example, a locus conversion of 7CN0020 can be developed when DNA sequences are introduced through backcrossing (Hallauer et al., 1988), with a parent of 7CN0020 utilized as the recurrent parent. Both naturally occurring and transgenic DNA sequences may be introduced through backcrossing techniques. A backcross conversion may produce a plant with a locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker assisted Selection in Backcross Breeding. In: Proceedings Symposium of the 30 Analysis of Molecular Data, August 1994, Crop Science Society of America, Corvallis, OR, where it is demonstrated that a backcross conversion can be made in as few as two backcrosses.

In another aspect a plant cell of an Essentially Derived Variety of 7CN0020 having one, two or three physiological and/or morphological characteristics which are different from those of 7CN0020 and which otherwise has all the physiological and morphological characteristics of 7CN0020 is described.

In another aspect the invention provides for a Canola hybrid variety 7CN0020. The invention also provides for a plurality of seeds of the new variety, plants produced from growing the seeds of the new variety 7CN0020, and progeny of any of these. Especially, progeny retaining one or more (or all) of the "distinguishing characteristics" or one or more (or all) of the "essential morphological and physiological characteristics" or essentially all physiological and morphological characteristics of 7CN0020 referred to herein, are encompassed herein as well as methods for producing these.

In one aspect, such progeny have (essentially) all the physiological and morphological characteristics of Canola hybrid variety 7CN0020 when grown under the same environmental conditions.

Further, Canola seeds produced on a plant grown from these seeds is provided.

In yet another embodiment of the invention, an Essentially Derived Variety of Canola hybrid variety 7CN0020 having one, two or three physiological and/or morphological characteristics which are different from those of 7CN0020 and which otherwise has all the physiological and morphological characteristics of 7CN0020, wherein a representative sample of seed of variety 7CN0020 has been deposited under Accession Number NCIMB 43759 is provided.

A plant having "(essentially) all the physiological and morphological characteristics" means a plant having the physiological and morphological characteristics when grown under the same environmental conditions of the plant from which it was derived, e.g. the progenitor plant, the parent, the recurrent parent, the plant used for tissue- or cell culture, etc. In certain embodiments the plant has all the physiological and morphological characteristics, except for certain characteristics mentioned, e.g. the characteristic(s) derived from a converted or introduced gene or trait and/or except for the characteristics which differ in an EDV. A plant have one or more "essential physiological and/or morphological characteristics" or one or more "distinguishing characteristics" refers to a plant having (or retaining) one or more of the characteristics mentioned in Table 1 when grown under the same environmental conditions that distinguish 7CN0020 from the most similar varieties, such as but not limited to oil content, protein content, erucic acid content, glucosinolate content, time to maturity, disease resistance/tolerance, in particular to the important diseases blackleg and clubroot, shatter resistance.

In other aspects, the invention provides for progeny of variety 7CN0020 such as progeny obtained by further breeding 7CN0020. Further breeding 7CN0020 includes selfing 7CN0020 one or more times and/or cross-pollinating 7CN0020 with another Canola plant or variety one or more times. In particular, the invention provides for progeny that retain all the essential morphological and physiological characteristics of 7CN0020 or that retain one or more of the distinguishing characteristics of the Canola type described further above and when grown under the same environmental conditions. In another aspect, the invention provides for vegetative reproductions of the variety and essentially derived varieties (EDVs) of 7CN0020.

Uses of Canola

Currently *Brassica napus* canola is being recognized as an increasingly important oilseed crop and a source of meal in many parts of the world. Therefore in one aspect the use of seeds of Canola hybrid variety 7CN0020 is described to grow a commercial crop. The oil as removed from the seeds commonly contains a lesser concentration of endogenously formed saturated fatty acids than other vegetable oils and is well suited for use in the production of salad oil or other food products or in cooking or frying applications. The oil also finds utility in industrial applications. Additionally, the meal component of the seeds can be used as a nutritious protein concentrate for livestock.

Canola oil has the lowest level of saturated fatty acids of all vegetable oils. "Canola" refers to rapeseed (*Brassica*) which (1) has an erucic acid (C22:1) content of at most 2 percent by weight based on the total fatty acid content of a seed, preferably at most 0.5 percent by weight and most preferably essentially 0 percent 5 by weight; and (2) produces, after crushing, an air-dried meal containing less than 30 micromoles (μmol) glucosinolates per gram of defatted (oil-free) meal. These types of rapeseed are distinguished by their edibility in comparison to more traditional varieties of the species. In one aspect the use of a Canola hybrid plant designated 7CN0020 is described to produce a commodity product comprising seed oil, meal, fibre or protein. Also the described is the use of a Canola hybrid plant designated 7CN0020 to produce crushed non-viable F2 seed and the use of such seeds to produce oil, meal, fibre or protein.

Diseases, Pests and Weeds

*Brassica*, in particular Canola is infected by a number of microbial diseases. The most important ones are listed below:

Bacterial
  bacterial leaf spot—*Pseudomonas syringae*
  bacterial soft rot—*Erwinia marginalis*
  bacterial soft rot *Pseudomonas*—*Pseudomonas marginalis*
  black rot—*Xanthomonas campestris*

Fungal
  *Alternaria* black spot—*Alternaria* spp.
  anthracnose—*Colletotrichum higginsianum*
  blackleg—*Leptosphaeria* maculans
  black mold rot—*Rhizopus stolonifer*
  black root—*Aphanomyces raphani*
  cercospora leaf spot—*Cercospora brassicicola*
  clubroot—*Plasmodiophora brassicae*
  downey mildew—*Peronospora parasitica*
  *Fusarium* wilt—*Fusarium avenaceum* and *F. oxysporum*.
  graymold—*Botrytis cinerea*
  light leaf spot—*Pyrenopeziza brassicae*
  *Phymatotrichum* root rot—Phymatotrichopsisomnivora
  phytophthora root rot—*Phytophthora megasperma*
  powdery mildew—*Erysiphe polygoni*
  ring spot—*Mycosphaerella brassicicola*
  root rot complex—*Rhizoctonia solani, Fusarium* and *Pythium* spp.
  seedling disease complex—*Rhizoctonia solani, Fusarium* and *Pythium* spp.
  sclerotinia white stem rot—*Sclerotinia sclerotiorum*
  southern blight—*Sclerotium rolfsii*
  *Verticillium* wilt—*Verticillium albo-atrum*
  white leaf spot and gray stem—*Pseudocercosporella capsellae*
  white rust and staghead—*Albugo candida*
  yellows—*Fusarium oxysporum*

Viral
  cauliflower mosaic virus
  radish mosaic virus
  turnip mosaic virus
  beet Western yellows virus Phytoplasma-Like
  aster yellows These diseases cause significant yield losses both in quantity and quality of the crop each year. Creation of disease tolerant or resistant canola cultivars has been an important goal for many of the Canadian canola breeding organizations. Conventional methods for control of diseases include chemical control, disease resistance and cultural control, each of which is described below.

Therefore in one aspect a method for the protection of a group of cultivated plants of Canola hybrid variety 7CN0020 in a field is described wherein the harmful microorganisms are controlled by the application of a composition comprising one or more microbicidal active ingredients. In one particular embodiment these active ingredients are selected from the group comprising azoxystrobin, benzovindiflupyr, boscalid, cyprodinil, fludioxonil, fluxapyroxad, fluopyram, ipfentrifluconazole, iprodione, isoflucypram, metalaxyl, mefenoxam, mefentrifluconazole, metconazole, penthiopyrad, picoxystrobin, propiconazole, prothioconazole, pyraclostrobin, pyraziflumid, pydiflumetofen, sedaxane, and tebuconazole. The active ingredients can be applied to Canola hybrid variety 7CN0020 as a foliar or seed treatment in customary formulations. The active ingredients can also be applied to the soil, where the Canola hybrid variety 7CN0020 will be seeded, is seeded, is growing, will be harvested or is harvested.

A significant number of weeds are present when growing Brassicaceae, in particular Canola.

The most important ones are listed below:
  ball mustard
  barnyard grass
  bluebur
  Canada thistle
  chickweed
  cleavers
  common peppergrass
  cow cockle
  field horsetail
  flixweed
  green foxtail
  green smartweed
  hare's ear mustard
  hemp nettle
  lady's thumb
  lamb's-quarters
  night-flowering catchfly
  quackgrass
  redroot pigweed
  Russian thistle
  shepherd's purse
  sow thistle
  stinkweed
  stork's bill
  volunteer canola
  wild buckwheat
  wild mustard
  wild oats
  wild rose
  wormseed mustard Conventional methods for control of weeds include mainly chemical or mechanical control.

The following herbicides are suitable for controlling weeds in Brassicaceae, in particular Canola: Carfentrazone (eg marketed as Aim™ by FMC), Clethodim (eg marketed as Centurion™ by BASF, as Arrow™ by ADAMA, as Shadow™ by Loveland, as Select™ by Ayrsta), Amitrol (eg marketed as Amitrol by Nufarm), Imazamox, Imazapyr (eg marketed as Ares™ or Odyssey™ or Solo™ by BASF), Quizalofop-p-ethyl (eg marketed as Assure II™ by Dupont, Yuma GL™ by Gowan), Triallate (eg marketed as Avadex™ by Gowan or Fortress™ by Gowan), Clopyralid (eg marketed as Eclipse III A™ by Corteva, Lontrel™ by Corteva), Ethalfluralin (eg marketed as Edge™ by Gowan), Trifluralin (eg marketed as Fortress™ by Gowan), Glyphosate (eg marketed as Roundup Weathermax,™ Roundup Ultra 2,™ Roundup Transorb™ by Monsanto), Saflufenacil (eg marketed as Heat™ by BASF), Glufosinate (eg marketed as Liberty™ by BASF), Quinclorac (eg marketed as Facet™ by BASF), Ethametsulfuron-methyl (eg marketed as Muster Toss-N-Go™ by Dupont), Tepraloxydim ((eg marketed as Equinox™ by BASF), Sethoxydim (eg marketed as Odyssey Ultra B™ or Poast Ultra™ by BASF), Diquat (eg marketed as Reglone™ by Syngenta), Trifluralin (eg marketed as Bonanza™ by Loveland, as Rival™ by Nufarm, as Treflan™ by Gowan).

Therefore in one aspect a method for the protection of a group of cultivated plants of Canola hybrid variety 7CN0020 in a field is described wherein the weeds are controlled by the application of a composition comprising at least one herbicidal active ingredients. In one particular embodiment these active ingredients are selected from the group comprising amitrol, carfentrazone, clethodim, clopyralid, dicamba, diquat, ethalfluralin, ethametsulfuron-methyl, florasulam, imazamox, imazapyr, glufosinate, glufosinate-ammonium, glyphosate, MCPA amine, MCPA ester, metsulfuron, quizalofop-p-ethyl, quinclorac, saflufenacil, triallate, and trifluralin. The active ingredients can be applied as a foliar, a pre-emergent, a post-emergent, a pre-harvest, a post-harvest, or a pre-seeding application in customary formulations.

A significant number of insect pests are present when growing Brassicaceae, in particular Canola. These pests cause significant yield losses both in quantity and quality of the crop each year. Conventional methods for control of diseases include chemical control, pest resistance and cultural control.

The most important pests are listed below:
*Autographia californica* Speyer
Aphids eg. *Brevicoryne brassicae, Hyadaphis erysimi*
*Loxostege sticticalis*
*Mamestra configurata*
*Ceutorhynchus* species eg *Ceutorhynchus obstrictis, Ceutorhynchus assimilis*
*Contarinia nasturtii* Kieffer
*Dicestra trifolii*
*Plutella xylostella*
*Phyllotrella* species eg *P. cruciferae, P. striolata*
*Lygus* species, eg *Lygus lineolaris*
*Vanessa cardui*
*Entomoscelis americana* Brown
*Delia* Species The following insecticides are suitable for controlling pests in Brassicaeae in particular Canola:
Chlorantraniliprole (eg marketed as Lumivia™ by E. I. Du Pont), cyantraniliprole (eg marketed as Lumiderm™ by E. I. Du Pont), Sulfoxaflor (eg marketed as Transform™ WG Corteva or as Rascendo™ by Syngenta), and spirotetramat.

Therefore in one aspect a method for the protection of a group of cultivated plants of Canola hybrid variety 7CN0020 in a field wherein the pests are controlled by the application of a composition comprising one or more insecticidal active ingredients. In one particular embodiment these active ingredients are selected from the group comprising broflanilide, carbaryl, carbofuran, chlorantraniliprole, chlorpyrifos, cypermethrin, cyclaniliprole, cyhalodiamide, clothianidin, deltamethrin, dimethoate, cyantraniliprole, cyhalothrin-lambda, imidacloprid, lambda-cyhalothrin, permethrin, sulfoxaflor, spirotetramate, tetraniliprole, and thiamethoxam. The active ingredients can be applied as a foliar or seed treatment in customary formulations.

Therefore in one aspect a method for the protection of a group of cultivated plants of Canola hybrid variety 7CN0020 in a field is provided wherein harmful microorganisms and/or pests are controlled by the application of a composition comprising one or more fungicidal or insecticidal active ingredients onto the seeds of said variety before seeding.

In one particular embodiment these active ingredients are selected from the group of comprising broflanilide, carbaryl, carbofuran, chlorantraniliprole, chlorpyrifos, cypermethrin, cyclaniliprole, cyhalodiamide, clothianidin, deltamethrin, dimethoate, cyantraniliprole, cyhalothrin-lambda, imidacloprid, lambda-cyhalothrin, permethrin, sulfoxaflor, spirotetramate, tetraniliprole, thiamethoxam azoxystrobin, benzovindiflupyr, boscalid, cyprodinil, fludioxonil, fluxapyroxad, fluopyram, ipfentrifluconazole, iprodione, isoflucypram, metalaxyl, mefenoxam, mefentrifluconazole, metconazole, penthiopyrad, picoxystrobin, propiconazole, prothioconazole, pyraclostrobin, pyraziflumid, pydiflumetofen, sedaxane, and tebuconazole.

Characteristics of 7CN0020

A canola hybrid needs to be homogenous and reproducible to be useful for the production of a commercial crop on a reliable basis. There are a number of analytical methods available to determine the phenotypic stability of a canola hybrid. The oldest and most traditional method of analysis is the observation of phenotypic traits. The data are usually collected in field experiments over the life of the canola plants to be examined. Phenotypic characteristics most often are observed for traits associated with seed yield, seed oil content, seed protein content, fatty acid composition of oil, glucosinolate content of meal, growth habit, lodging resistance, plant height, shatter resistance, etc. In addition to phenotypic observations, the genotype of a plant can also be examined. A plant's genotype can be used to identify plants of the same variety or a related variety. For example, the genotype can be used to determine the pedigree of a plant. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (OAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). The variety of the present invention has shown uniformity and stability for all traits, as described in the following variety description information. The variety has been increased with continued observation for uniformity. 7CN0020 is an early maturing, high yielding, glufosinate resistant *Brassica napus* canola hybrid having a resistant (R) rating for blackleg and for clubroot. Its oil content is 1.7% higher than WCC/RRC checks. It can be distinguished from the checks by the leaf length, petiole length, and plant height at maturity. Table 1 provides data on morphological, agronomic, and quality traits for 7CN0020. When preparing the detailed phenotypic information that follows, plants of the new 7CN0020 variety were observed while being grown using conventional agronomic practices. For comparative purposes, canola plants of canola varieties PA8CN152 and PR6CN666 were similarly grown in a replicated experiment. Observations were recorded on various morphological traits for the hybrid 7CN0020 and comparative check cultivars. (See Table 1.) Hybrid 7CN0020 can be advantageously used in accordance with the breeding methods described herein and those known in the art to produce hybrids and other progeny plants retaining desired trait combinations of 7CN0020. This invention is thus also directed to methods for producing a canola plant by crossing a first parent canola plant with a second parent canola plant wherein either the first or second parent canola plant is canola variety 7CN0020. Further, both first and second parent canola plants can come from the canola variety 7CN0020. Either the first or the second parent plant may be male sterile. Still further, this invention also is directed to methods for producing a 7CN0020-derived canola plant by crossing canola variety 7CN0020 with a second canola plant and growing the progeny seed, and repeating the crossing and growing steps with the canola 7CN0020-derived plant from 1 to 2 times, 1 to 3 times, 1 to 4 times, or 1 to 5 times. Thus, any such methods using the canola variety 7CN0020 are part of this invention: open pollination, selfing, backcrosses, hybrid production, crosses to populations, and the like. All plants produced using canola variety 7CN0020 as a parent are within the scope of this invention, including plants derived from canola variety 7CN0020. This includes canola lines derived from 7CN0020 which include components for either male sterility or for restoration of fertility. Advantageously, the canola variety is used in crosses with other, different, canola plants to produce first generation (F1) canola hybrid seeds and plants with superior characteristics. The invention also includes a single-gene conversion of 7CN0020. A single-gene conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to, fertility restoration, fatty acid profile modification, other nutritional enhancements, industrial enhancements, disease resistance, insect resistance, herbicide resistance and yield enhancements. The trait of interest is transferred from the donor parent to the recurrent parent, in this case, the canola plant disclosed herein. Single-gene traits may result from the transfer of either a dominant allele or a recessive allele. Selection of progeny containing the trait of interest is done by direct selection for a trait associated with a dominant allele. Selection of progeny for a trait that is transferred via a recessive allele will require growing and selfing the first backcross to determine which plants carry the recessive alleles. Recessive traits may require additional progeny testing in successive backcross generations to determine the presence of the gene of interest. It should be understood that the canola variety of the invention can, through routine manipulation by cytoplasmic genes, nuclear genes, or other factors, be produced in a male-sterile or restorer form as described in the references discussed earlier. Such embodiments are also within the scope of the present claims. Canola variety 7CN0020 can be manipulated to be male sterile by any of a number of methods known in the art, including by the use of mechanical methods, chemical methods, self-incompatibility (SI), cytoplasmic male sterility (CMS) (either Ogura or another system}, or nuclear male sterility (NMS). The term "manipulated to be male sterile" refers to the use of any available techniques to produce a male sterile version of canola variety 7CN0020. The male sterility may be either partial or complete male sterility. This invention is also directed to F1 hybrid seed and plants produced by the use of Canola variety 7CN0020. Canola variety 7CN0020 can also further comprise a component for fertility restoration of a male sterile plant, such as an Rf restorer gene. In this case, canola variety 7CN0020 could then be used as the male plant in hybrid seed production. This invention is also directed to the use of 7CN0020 in tissue culture. As used herein, the term plant includes plant protoplasts, plant cell tissue cultures from which canola plants can be regenerated, plant calli, plant clumps, and plant cells that are intact in plants or parts of plants, such as embryos, pollen, ovules, seeds, flowers, kernels, ears, cobs, leaves, husks, stalks, roots, root tips, anthers, silk and the like. Pauls, et al., (2006) (Canadian J of Botany 84(4):668-678) confirmed that tissue culture as well as microspore culture for regeneration of canola plants can be accomplished successfully. Chuong, et al., (1985) "A Simple Culture Method for *Brassica* Hypocotyl Protoplasts", Plant Cell Reports 4:4-6; Barsby, et al., (Spring 1996) "A Rapid and Efficient Alternative Procedure for the Regeneration of Plants from Hypocotyl Protoplasts of *Brassica napus*", Plant Cell Reports; Kartha, et al., (1974) "In vitro Plant Formation from Stem Explants of Rape", Physiol. Plant 31:217-220; Narasimhulu, et al., (Spring 1988) "Species Specific Shoot Regeneration Response of Cotyledonary Explants of Brassicas", Plant Cell Reports; Swanson, (1990) "Microspore Culture in *Brassica*", Methods in Molecular Biology 6(17): 159; "Cell Culture techniques and Canola improvement" J. Am. Oil Chem. Soc. 66(4):455-56 (1989). Thus, it is clear from the literature that the state of the art is such that these methods of obtaining plants are, and were, "conventional" in the sense that they are routinely used and have a very high rate of success.

The utility of canola variety 7CN0020 also extends to crosses with other species. Commonly, suitable species will be of the family Brassicaceae. The advent of new molecular biological techniques has allowed the isolation and characterization of genetic elements with specific functions, such as encoding specific protein products.

Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species, or from the same species that are inserted into the genome using transformation are referred to herein collectively as "transgenes". Over the last fifteen to twenty years several methods for producing transgenic plants have been developed, and the present invention, in particular embodiments, also relates to transformed versions of the claimed canola variety 7CN0020.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick, and Genetic Transformation for the improvement of Canola World Conf, Biotechnol. Fats and Oils Ind. 43-46 (1988). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson, Eds. (CRC Press, Inc., Boca Raton, 1993) pages 89-119. The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements. A genetic trait which has been engineered into a particular canola plant using transformation techniques could be moved into another line using traditional breeding techniques that are well known in the plant breeding arts. For example, a backcrossing approach could be used to move a transgene from a transformed canola plant to an elite inbred line and the resulting progeny would comprise a transgene. Also, if an inbred line was used for the transformation then the transgenic plants could be crossed to a different line in order to produce a transgenic hybrid canola plant. As used herein, "crossing" can refer to a simple X by Y cross, or the process of backcrossing, depending on the context.

Various genetic elements can be introduced into the plant genome using transformation. These elements include but are not limited to genes; coding sequences; inducible, constitutive, and tissue specific promoters; enhancing sequences; and signal and targeting sequences. See U.S. Pat. No. 6,222,101. With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, (1981) Anal. Biochem. 114: 92-96. A genetic map can be generated, primarily via conventional Restriction Fragment Length Polymorphisms (RFLP), Polymerase Chain Reaction (PCR) analysis, Simple Sequence Repeats (SSR), and Single Nucleotide Polymorphisms (SNPs), which identifies the approximate chromosomal location of the integrated DNA molecule coding for the foreign protein. For exemplary methodologies in this regard, see, Glick and Thompson, METHODS IN PLANT MOLECULAR BIOLOGY AND BIOTECHNOLOGY 269-284 (CRC Press, Boca Raton, 1993). Map lo information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, SNP, and sequencing, all of which are conventional techniques. Likewise, by means of the present invention, plants can be genetically engineered to express various phenotypes of agronomic interest. Exemplary transgenes implicated in this regard include, but are not limited to, those categorized below.

1. Genes that confer resistance to pests or disease and that encode:
    (A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones, et al., (1994) Science 266:789 (cloning of the tomato Cf-9 gene for resistance to *Cladosporium fulvum*); Martin, et al., (1993) Science 262:1432 (tomato Pto gene for resistance to *Pseudomonas syringae* pv. tomato encodes a protein kinase); Mindrinos, et al., (1994) Cell 78: 1089 (*Arabidopsis* RSP2 gene for resistance to *Pseudomonas syringae*); McDowell and Woffenden, (2003) Trends Biotechnol. 21(4):178-83 and Toyoda, et al., (2002) Transgenic Res. 11(6):567-82. A plant resistant to a disease is one that is more resistant to a pathogen as compared to the wild type plant.
    (B) A gene conferring resistance to fungal pathogens, such as oxalate oxidase or oxalate decarboxylase (Zhou, et al., (1998) Pl. Physiol. 117(1):33-41).
    (C) A *Bacillus thuringiensis* (Bt) protein, a derivative thereof or a synthetic polypeptide modeled thereon. See, for example, Geiser, et al., (1986) Gene 48:109, who disclose the cloning and nucleotide sequence of a Bf deltaendotoxin gene. Moreover, DNA molecules encoding delta-endotoxin genes can be purchased from American Type Culture Collection (Manassas, VA), for example, under ATCC Accession Numbers 40098, 67136, 31995 and 31998. Other examples of *Bacillus thuringiensis* transgenes being genetically engineered are given in the following patents and patent applications: U.S. Pat. Nos. 5,188,960; 5,689,052; 5,880,275; WO 91/114778; WO 99/31248; WO 01/12731; WO 99/24581; WO 97/40162 and U.S. application Ser. Nos. 10/032,717; 10/414,637; and Ser. No. 10/606,320.
    (D) An insect-specific hormone or pheromone such as an ecdysteroid and juvenile hormone, a variant thereof, a mimetic based thereon, or an antagonist or agonist thereof. See, for example, the disclosure by Hammock, et al., (1990) Nature 344:458, of baculovirus expression of cloned juvenile hormone esterase, an inactivator of juvenile hormone.
    (E) An insect-specific peptide which, upon expression, disrupts the physiology of the affected pest. For example, see the disclosures of Regan, (1994) J. Biol. Chem. 269:9 (expression cloning yields DNA coding for insect diuretic hormone receptor) and Pratt, et al., (1989) Biochem. Biophys. Res. Comm. 163:1243 (an allostatin is identified in *Diploptera puntata*); Chattopadhyay, et al., (2004) Critical Reviews in Microbiology 30(1):33-54 2004; Zjawiony, (2004) J Nat Prod 67(2):300-310; Carlini and Grossi-de-Sa, (2002) Toxicon 40(11):1515-1539; Ussuf, et al., (2001) Curr Sci. 80(7):84 7-853 and Vasconcelos and Oliveira, (2004) Toxicon 44(4):385-403. See also, U.S. Pat. No. 5,266, 317 to Tomalski, et al., who disclose genes encoding insect-specific, paralytic neurotoxins.
    (F) An enzyme responsible for a hyperaccumulation of a monterpene, a sesquiterpene, a steroid, hydroxamic acid, a phenylpropanoid derivative or another non-protein molecule with insecticidal activity.
    (G) An enzyme involved in the modification, including the posttranslational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application Number WO 93/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) Insect Biochem. Molec. Biol. 23:691, who teach the nucleotide sequence of a cDNA encoding tobacco hookworm chitinase, and Kawalleck et al., (1993) Plant Molec. Biol. 21:673, who provide the nucleotide sequence of the parsley ubi4-2 polyubiquitin gene, U.S. patent application Ser. Nos. 10/389,432, 10/692,367 and U.S. Pat. No. 6,563,020.

(H) A molecule that stimulates signal transduction. For example, see the disclosure by Botella, et al., (1994) Plant Molec. Biol. 24:757, of nucleotide sequences for mung bean calmodulin cDNA clones, and Griess, et al., (1994) Plant Physiol. 104:1467, who provide the nucleotide sequence of a maize calmodulin cDNA clone.

(I) A hydrophobic moment peptide. See, PCT Application Number W095/16776 and U.S. Pat. No. 5,580,852 (disclosure of peptide derivatives of Tachyplesin which inhibit fungal plant pathogens) and PCT Application Number W095/18855 and U.S. Pat. No. 5,607,914 (teaches synthetic antimicrobial peptides that confer disease resistance).

(J) A membrane permease, a channel former or a channel blocker. For example, see the disclosure by Jaynes, et al., (1993) Plant Sci. 89:43, of heterologous expression of a cecropin-beta lytic peptide analog to render transgenic tobacco plants resistant to *Pseudomonas solanacearum*.

(K) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., (1990) Ann. Rev. Phytopathol. 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(L) An insect-specific antibody or an immunotoxin derived therefrom. Thus, an antibody targeted to a critical metabolic function in the insect gut would inactivate an affected enzyme, killing the insect. Cf Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(M) A virus-specific antibody. See, for example, Tavladoraki, et al., (1993) Nature 366:469, who show that transgenic plants expressing recombinant antibody genes are protected from virus attack.

(N) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) Bio/Technology 10: 1436. The cloning and characterization of a gene which encodes a bean endopolygalacturonase-inhibiting protein is described by Toubart, et al., (1992) Plant J. 2:367. A developmental-arrestive protein produced in nature by a plant. For example, Logemann, et al., (1992) Bio/Technology 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) Current Biology 5(2):128-131, Pieterse and Van Loon, (2004) Curr. Opin. Plant Bio 7(4):456-64 and Somssich, (2003) *Cell* 113(7):815-6.

(P) Antifungal genes (Cornelissen and Melchers, (1993) Pl. Physiol. 101:709-712 and Parijs, et al., (1991) Planta 183:258-264 and Bushnell, et al., (1998) Can. J. of Plant Path. 20(2):137-149. Also see, U.S. patent application Ser. No. 09/950,933.

(Q) Detoxification genes, such as for fumonisin, beauvericin, moniliformin and zearalenone and their structurally related derivatives. For example, see, U.S. Pat. No. 5,792,931.

(R) Cystatin and cysteine proteinase inhibitors. See, U.S. patent application Ser. No. 10/947,979.

(S) Defensin genes. See, W003/000863 and U.S. patent application Ser. No. 10/178,213. (U) Genes that confer resistance to *Phytophthora* Root Rot, such as the *Brassica* equivalents of the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al, (1995) *Phytophthora* Root Rot Resistance Gene Mapping in Soybean, Plant Genome IV Conference, San Diego, CA 2. Genes that confer resistance to a herbicide, for example:

(A) A herbicide that inhibits the growing point or meristem, such as an imidazalinone or a sulfonylurea. Exemplary genes in this category code for mutant ALS and AHAS enzyme as described, for example, by Lee, et al., (1988) EMBO J. 7:1241, and Miki, et al., (1990) Theor. Appl. Genet. 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; and international publication WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. See also, U.S. Pat. No. 7,405,074, and related applications, which disclose compositions and means for providing glyphosate resistance. U.S. Pat. No. 5,627,061 to Barry, et al., also describes genes encoding EPSPS enzymes. See also, U.S. Pat. Nos. 6,566,587; 6,338,961; 6,248,876 81; 6,040,497; 5,804,425; 5,633,435; 5,145,783; 4,971, 908; 5,312,910; 5,188,642; 4,940,835; 5,866,775; 6,225,114 81; 6,130,366; 5,310,667; 4,535,060; 4,769, 061; 5,633,448; 5,510,471; Re. 36,449; RE 37,287 E; and 5,491,288; and international publications EP1173580; WO 01/66704; EP1173581 and EP1173582. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyltransferase gene is provided in European Application Number 0 242 246 to Leemans, et al., De Greef, et al., (1989) Bio/Technology 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 81 and 5,879,903. Exemplary of genes conferring resistance to phenoxy propionic acids and cyclohexones, such as sethoxydim and haloxyfop, are the Acc1-S1, Acc1-S2 and Acc1-S3 genes described by Marshall, et al., (1992) Theor. Appl. Genet. 83:435. See also, U.S. Pat. Nos. 5,188,642; 5,352,605; 5,530,196; 5,633,435; 5,717,084; 5,728,925; 5,804,425 and Canadian Patent Number 1,313,830.

(C) A herbicide that inhibits photosynthesis, such as a triazine (psbA and gs+ genes) and a benzonitrile (nitrilase gene). Przibilla, et al., (1991) Plant Cell 3: 169, describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Numbers 53435, 67441 and 67442. Cloning and expression of DNA coding fora glutathione S-transferase is described by Hayes, et al., (1992) Biochem. J. 285:173.

(D) Acetohydroxy acid synthase, which has been found to make plants that express this enzyme resistant to multiple types of herbicides, has been introduced into a variety of plants (see, e.g., Hattori, et al., (1995) Mol Gen Genet 246:419). Other genes that confer tolerance to herbicides include: a gene encoding a chimeric protein of rat cytochrome P4507A1 and yeast NADPH-cytochrome P450 oxidoreductase (Shiota, et al., (1994) Plant Physiol 106:17), genes for glutathione reductase and superoxide dismutase (Aono, et al., (1995) Plant Cell Physiol 36: 1687, and genes for various phosphotransferases (Datta, et al., (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 81; 6,282,837 81; and 5,767,373; and international publication WO 01/12825.

3. Transgenes that confer or contribute to an altered grain characteristic, such as:

(A) Altered fatty acids, for example, by
(1) Down-regulation of stearoyl-ACP desaturase to increase stearic acid content of the plant. See, Knultzon, et al., (1992) Proc. Natl. Acad. Sci. USA 89:2624 and WO99/64579 (Genes for Desaturases to Alter Lipid Profiles in Corn),
(2) Elevating oleic acid via FAD-2 gene modification and/or decreasing linolenic acid via FAD-3 gene modification (see, U.S. Pat. Nos. 6,063,947; 6,323,392; 6,372,965 and WO 93/11245),
(3) Altering conjugated linolenic or linoleic acid content, such as in WO 01/12800,
(4) Altering LEC1, AGP, Dek1, Superal1, mil ps, various Ipa genes such as Ipa1, Ipa3, hpt or hggt. For example, see WO 02/42424, WO 98/22604, WO 03/011015, U.S. Pat. Nos. 6,423,886, 6,197,561, 6,825,397, US Patent Application Publication Numbers 2003/0079247, 2003/0204870, W002/057439, W003/011015 and Rivera-Madrid, et al., (1995) Proc. Natl. Acad. Sci. 92:5620-5624.

(B) Altered phosphorus content, for example, by the
(1) Introduction of a phytase-encoding gene would enhance breakdown of phytate, adding more free phosphate to the transformed plant. For example, see, Van Hartingsveldt, et al., (1993) Gene 127:87, for a disclosure of the nucleotide sequence of an Aspergillus niger phytase gene.
(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) Maydica 35:383 and/or by altering inositol kinase activity as in WO 02/059324, US Patent Application Publication Number 2003/0009011, WO 03/027243, US Patent Application Publication Number 2003/0079247, WO 99/05298, U.S. Pat. Nos. 6,197,561, 6,291,224, 6,391, 348, W02002/059324, US Patent Application Publication Number 2003/0079247, W098/45448, W099/ 55882, W001/04147.

(C) Altered carbohydrates effected, for example, by altering a gene for an enzyme that affects the branching pattern of starch, a gene altering thioredoxin. (See, U.S. Pat. No. 6,531,648). See, Shiroza, et al., (1988) J. Bacterial 170:810 (nucleotide sequence of Streptococcus mutans fructosyltransferase gene), Steinmetz, et al., (1985) Mol. Gen. Genet. 200:220 (nucleotide sequence of Bacillus subtilis levansucrase gene), Pen, et al., (1992) Bio/Technology 10:292 (production of transgenic plants that express Bacillus licheniformis alpha amylase), Elliot, et al., (1993) Plant Molec Biol 21:515 (nucleotide sequences of tomato invertase genes), Sogaard, et al., (1993) J. Biol. Chem. 268:22480 (site directed mutagenesis of barley alpha-amylase gene) and Fisher, et al., (1993) Plant Physiol 102: 1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP).

4. Genes that control pollination, hybrid seed production, or male-sterility: There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum specific promoter and with the application of the chemical N-Ac-PPT (WO01/29237).

(B) Introduction of various stamen-specific promoters (WO 92/13956, WO 92/13957).

(C) Introduction of the barnase and the barstar gene (Paul, et al., (1992) Plant Mol. Biol. 19:611-622). For additional examples of nuclear male and female sterility systems and genes, see also, U.S. Pat. Nos. 5,859,341; 6,297,426; 5,478,369; 5,824,524; 5,850,014 and 6,265,640. Also see, U.S. Pat. No. 5,426,041 (invention relating to a method for the preparation of a seed of a plant comprising crossing a male sterile plant and a second plant which is male fertile), U.S. Pat. No. 6,013,859 (molecular methods of hybrid seed production) and U.S. Pat. No. 6,037,523 (use of male tissue-preferred regulatory region in mediating fertility).

5. Genes that create a site for site specific DNA integration. This includes the introduction of FRT sites that may be used in the FLP/FRT system and/or Lox sites that may be used in the Cre/Loxp system. For example, see, Lyznik, et al., (2003) "Site-Specific Recombination for Genetic Engineering in Plants", Plant Cell Rep 21:925-932 and WO 99/25821. Other systems that may be used include the Gin recombinase of phage Mu (Maeser, et al., 1991), the Pin recombinase of *E. coli* (Enomoto, et al., 1983), and the R/RS system of the pSR 1 plasmid (Araki, et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see, WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO2000060089, WO2001026459, WO2001035725, WO2001034726, WO2001035727, WO2002015675, WO2003013227, WO2001036444, WO2002017430, WO2003013228, WO2001036597, WO2002077185, WO2003014327, WO2001036598, WO2002079403, WO2004031349, WO2004076638, WO9809521 and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. Nos. 10/817,483 and 09/545,334 where cytokinin expression is modified resulting in plants with increased stress tolerance, such as drought tolerance, and/or increased yield. Also see WO00202776, WO03052063, JP2002281975, U.S. Pat. No. 6,084,153, WO0164898, U.S. Pat. Nos. 6,177,275 and 6,107,547 (enhancement of nitrogen utilization and altered nitrogen responsiveness). For ethylene alteration, see, US Patent Application Publication Numbers 2004/0128719, 2003/0166197 and WO200032761. For plant transcription factors or transcriptional regulators of abiotic stress, see e.g., US Patent Application Publication Number 2004/0098764 or US Patent Application Publication Number 2004/0078852. Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/

38560, W001/21822 (VRN1), W000/44918 (VRN2), W099/49064 (GI), W000/46358 (FRI), W097/29123, U.S. Pat. Nos. 6,794,560, 6,307,126 (GAi), W099/09174 (O8 and Rht), and W02004076638 and W02004031349 (transcription factors).

Seed Cleaning

This invention is also directed to methods for producing cleaned canola seed by cleaning seed of variety 7CN0020. "Cleaning a seed" or "seed cleaning" refers to the removal of foreign material from the surface of the seed. Foreign material to be removed from the surface of the seed includes but is not limited to fungi, bacteria, insect material, including insect eggs, larvae, and parts thereof, and any other pests that exist on the surface of the seed. The terms "cleaning a seed" or "seed cleaning" also refer to the removal of any debris or low quality, infested, or infected seeds and seeds of different species that are foreign to the sample.

This invention is also directed to produce subsequent generations of seed from seed of variety 7CN0020, harvesting the subsequent generation of seed; and planting the subsequent generation of seed.

Seed Treatment "Treating a seed" or "applying a treatment to a seed" refers to the application of a composition to a seed as a coating or otherwise. The composition may be applied to the seed in a seed treatment at any time from harvesting of the seed to sowing of the seed. The composition may be applied using methods including but not limited to mixing in a container, mechanical application, tumbling, spraying, misting, and immersion. Thus, the composition may be applied as a slurry, a mist, or a soak. The composition to be used as a seed treatment can be a pesticide, fungicide, insecticide, or antimicrobial. For a general discussion of techniques used to apply fungicides to seeds, see "Seed Treatment," 2d ed., (1986), edited by K. A Jeffs (chapter 9). Industrial Applicability The seed of the 7CN0020 variety, the plant produced from such seed, various parts of the 7CN0020 hybrid canola plant or its progeny, a canola plant produced from the crossing of the 7CN0020 variety, and the resulting seed, can be utilized in the production of an edible vegetable oil or other food products in accordance with known techniques. The remaining solid meal component derived from seeds can be used as a nutritious livestock feed.

DEPOSITS

Applicant(s) have made a deposit of at least 2500 seeds of 7CN0020 Canola hybrid variety with NCIMB Ltd, Ferguson Building, Craibstone Estate, Bucksburn, Aberdeen, AB21 9YA Scotland. The seeds of 7CN0020 Canola hybrid variety were deposited on Apr. 6, 2021 with NCIMB under Accession Number NCIMB 43759. The seeds were taken from the seed stock maintained by BASF Canada Inc. prior to the filing date of this application. Access to these deposits will be available during the pendency of the application to the Commissioner of Patents and Trademarks and persons determined by the Commissioner to be entitled thereto upon request. Upon allowance of any claims in the application, the Applicant will make available to the public, pursuant to 37 C.F.R. § 1.808, sample(s) of the deposit of at least 2500 seeds of 7CN0020 Canola hybrid variety all which are with NCIMB Ltd, Ferguson Building, Craibstone Estate, Bucksburn, Aberdeen, AB21 9YA Scotland. These deposits of seed of 7CN0020 Canola hybrid variety will be maintained in the NCIMB depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of NCIMB, including providing an indication of the viability of the sample upon deposit. Applicant has no authority to waive any restrictions imposed by law on the transfer of biological material or its transportation in commerce. Applicant(s) do not waive any infringement of their rights granted under this patent or rights applicable to canola hybrid 7CN0020 or of the parental Canola varieties under the Plant Breeders' Rights Act (S.C. 1990, c.20).

EXAMPLES

The invention is illustrated by the following examples. However the invention is not limited to the examples.

WCC/RCC is the abbreviation for the Western Canadian Canola Rapeseed Recommending Committee.

Example 1

Summary of Variety Characteristics

7CN0020 is an early-maturing canola hybrid (2.6 days later than the average of checks) which is suitable for all growing zones in Canada providing high yields. 7CN0020 is reduced in pod shatter allowing both straight cutting or delayed swathing for harvest. In addition the 7CN0020 provides strong lodging resistance. The pollination control used in 7CN0020 is the nuclear genetic male sterility system based on barstar/barnase (SeedLink™, BASF). Due to the early maturation 7CN0020 might be seeded later in the season in case conditions for seeding due to for example weather conditions are challenging and seeding needs to be delayed. 7CN0020 is of medium height and provides strong lodging resistance. In addition to be rated as blackleg-resistant 7CN0020 possesses also the agronomic trait of being clubroot resistant to predominant clubroot pathotypes identified in Canada in 2017.

7CN0020 has a black seed coat color. The oil content is 49.8% on a whole dry seed basis. The protein content is 43.7% on a whole dry seed basis. Glucosinolates content of 7CN0020 is 9.58 umol per gram of whole seed at a moisture of 8.5%, therefore low.

Leaf length, petiole length, and plant height at maturity may be considered as further variety distinguishing characteristics. 7CN0020 is tolerant to the herbicide Glufosinate and salts thereof, e.g. glufosinate ammonium.

TABLE 1

| Trait Code | Trait | Mean of 7CN0020 | Description of 7CN0020 | Mean of PA8CN152 | Mean of PR6CN666 |
|---|---|---|---|---|---|
| 1.1 | Botanical name | | *Brassica napus* L. | | |
| 1.2 | Season type | | Spring | | |
| 1.3 | CSGA recognized type of variety | | Hybrid | | |

TABLE 1-continued

| Trait Code | Trait | Mean of 7CN0020 | Description of 7CN0020 | Mean of PA8CN152 | Mean of PR6CN666 |
|---|---|---|---|---|---|
| 1.4 | Pollination control | | Nuclear genetic male sterility (Seedlink ™) | | |
| 2.3 | Stem anthocyan intensity (1 = absent or very weak, 3 = weak, 5 = medium, 7 = strong, 9 = very strong) | 1 | | 1 | 1.5 |
| 2.4 | Leaf type (1 = petiolate, 9 = lyrate) | 1 | | 1 | 1 |
| 2.6 | Leaf length (3 = short, 5 = medium, 7 = long) | 7 | | 2 | 3 |
| 2.7 | Leaf width (3 = narrow, 5 = medium, 7 = wide) | 6 | | 4 | 3 |
| 2.8 | Leaf colour at 5-leaf stage (1 = light green, 2 = medium green, 3 = dark green, 4 = blue-green) | 2.3 | | 3.2 | 2.3 |
| 2.12 | Leaf lobe development (observe fully developed upper stem leaves): (1 = absent or very weak, 3 = weak, 5 = medium, 7 = strong, 9 = very strong) | 8 | | 3 | 8 |
| 2.13 | Number of leaf lobes | 4.4 | | 1.7 | 4.3 |
| 2.15 | Petiole length (lobed varieties only) (3 = short, 5 = medium, 7 = long) | 4 | | 2 | 3 |
| 2.16 | Leaf margin shape (1 = undulating, 2 = rounded, 3 = sharp) | 2 | | 2 | 2 |
| 2.17 | Leaf margin indentation (1 = absent or very weak (very shallow), 3 = weak (shallow), 5 = medium, 7 = strong (deep), 9 = very strong (very deep)) | 5.3 | | 3.3 | 4.3 |
| 2.18 | Leaf attachment to stem (1 = complete clasping, 2 = partial clasping, 3 = non-clasping) | 2 | | 2 | 2 |
| 3.1 | Time to flowering (number of days from planting to 50% of plants showing one or more open flowers) | 42 | | 40 | 45 |
| 3.2 | Plant height at maturity (3 = short, 5 = medium, 7 = tall) | 6 | | 6 | 6 |
| 3.4 | Flower bud location (1 = buds above most recently opened flowers, 9 = buds below most recently opened flowers) | 1 | | 1 | 1 |
| 3.5 | Petal colour (observe on frist day of flowering) (1 = white, 2 = light yellow, 3 = medium yellow, 4 = dark yellow, 5 = orange, 6 = other) | 3 | | 3 | 3 |
| 3.6 | Petal length (3 = short, 5 = medium, 7 = long) | 5 | | 5 | 5 |
| 3.7 | Petal width (3 = narrow, 5 = medium, 7 = wide) | 5 | | 4 | 4 |
| 3.11 | Anther fertility (measured by pollen production) (1 = sterile, 9 = all anthers shedding pollen) | 9 | | 1 (50% sterile) | 9 |
| 3.12 | Pod (silique) length (1 = short (<7 cm), 5 = medium (7 to 10 cm), 9 = long (>10 cm) | 1 | | 1 | 1 |

TABLE 1-continued

| Trait Code | Trait | Mean of 7CN0020 | Description of 7CN0020 | Mean of PA8CN152 | Mean of PR6CN666 |
|---|---|---|---|---|---|
| 3.14 | Pod (silique) angle (1 = erect, 3 = semi-erect, 5 = horizontal, 7 = slightly drooping, 9 = drooping) | 4.3 | | 2.0 | 5.5 |
| 3.15 | Pod (silique) beak length (3 = short, 5 = medium, 7 = long) | 3 | | 2 | 3 |
| 3.16 | Pedicel length (3 = short, 5 = medium, 7 = long) | 3 | | 2 | 3 |
| 3.17 | Time to maturity (number of days from planting to physiological maturity) | 96 | | 97 | 96 |
| 4.1 | Seed coat colour (1 = black, 2 = brown, 3 = tan, 4 = yellow, 5 = mixed, 6 = other) | 1 | | 1 | 1 |
| 5.1 | Shatter Resistance (1 = not tested, 3 = poor, 5 = fair, 7 = good, 9 = does not shatter) | 5.3 | | 3.7 | 7.0 |
| 5.2 | Lodging resistance (1 = not tested, 3 = poor, 5 = fair, 7 = good, 9 = excellent) | 5.3 | | 6.0 | 4.5 |
| 6.3 | Blackleg (*Leptospheria maculans*/Phoma ligam) (1 = resistant, 3 moderately resistant, 5 = moderately susceptible, 7 = susceptible, 9 = highly susceptible) | 1 | | 1 | 1 |
| 6.4 | Club Root (*Plasmodiophora brassicae* Woronin) (1 = resistant, 3 moderately resistant, 5 = moderately susceptible, 7 = susceptible, 9 = highly susceptible) | 1 | | 1 | 7 |
| 7.1 | Resistance to herbicides | | Glufosinate ammonium | | |
| 8.1 | Oil content (percentage, whole dry seed basis) | 49.8 | | 50.5 | 48.1 |
| 8.2.6 | Erucic acid (C22:1) as percentage of total fatty acids in seed oil | 0.01 | | 0.01 | 0.00 |
| 8.5 | Protein content (percentage, whole oil-free dry seed basis) | 43.7 | | 44.6 | 46.4 |
| 8.7 | Glucosinolates content (μmol of total glucosinolates per gram whole seed, 8.5% moisture basis) (1 = very low (<10 μmol per gram, 2 = low (10-15 μmol per gram), 3 = medium (15-20 μmol per gram), 4 = high (>20 μmol per gram) | 9.6 | | 15.3 | 10.40 |

Example 2

7CN0020 was tested in 2017 and 2018 trials following WCC/RCC guidelines. WCC/RRC guidelines were followed for analyzing quality parameters. Yield and agronomic traits were recorded and seed samples were collected and were analyzed for quality traits such as oil and protein percent, total whole seed glucosinolates, and eruic acid content. Protein and oil content was according to WCC/RRC criteria. One station represents one trial at a certain location in a specific year.

Yield is expressed as percentage of the yield of the standard of the Canola hybrids 45H29 (Pioneer Hi-Bred) and 5440 (BASF Canada Inc.). Oil, protein and saturate fatty acid content were according to WCC/RCC criteria. Maturity allows wide adaptation across all zones. Glucosinolates content was 11.3 umoles/g whole seed at 8.5% moisture (all zones). Erucic acid content was 0.01% (all zones).

TABLE 2

| | Yield (% of 5440 & 45H29) | | | |
|---|---|---|---|---|
| | Overall | Short season zone | Mid season zone | Long season zone |
| Yield in Trials 2017 | 115.4 | 113.0 | 118.8 | 112.8 |
| Number of Station Years | 14 | 3 | 6 | 5 |
| Yield in Trials 2018 | 104.4 | 100.0 | 105.7 | 106.6 |
| Number of Station Years | 22 | 6 | 9 | 7 |

Example 3

Blackleg Resistance

Blackleg resistance is rated on a scale of 0 to 5: a plant with zero rating is completely immune to disease while a plant with "5" rating is dead due to blackleg infection. Plants in blackleg trials are rated at the 5.2 stage on the Harper and Berkenkamp scale and that evaluation of disease reaction is based on the extent of the infection throughout the stem. This was evaluated by cutting open the stem at the site of the canker.

Tests were rated using a 0-5 scale, as follows:

0—no diseased tissue visible in the cross-section
1—Diseased tissue occupies up to 25% of cross-section
2—Diseased tissue occupies 26-50% of cross-section
3—Diseased tissue occupies 51-75% of cross-section
4—Diseased tissue occupies more than 75% of cross-section with little or no constriction of affected tissues
5—Diseased tissue occupies 100% of cross-section with significant constriction of affected tissues; tissue dry and brittle; plant dead Canola variety "Westar" is included as an entry/control in each blackleg trial. Tests are considered valid when the mean rating for Westar is greater than or equal to 2.6 and less than or equal to 4.5. (In years when there is poor disease development in Western Canada the WCC/RRC may accept the use of data from trials with a rating for Westar exceeding 2.0.). 7CN0020 has an "R" rating for Blackleg (18.0% of Westar) according to the 2017 and 2018 trials described in example 2.

The invention claimed is:

1. A plant or part thereof of a Canola hybrid variety designated 7CN0020, wherein a representative sample of seed of that variety has been deposited under Accession Number NCIMB 43759, wherein the part thereof comprises at least one cell of Canola hybrid variety designated 7CN0020.

2. A method for the protection of a group of cultivated plants of the plant of claim 1, comprising one or more of:
   (a) applying a composition comprising one or more herbicidal active ingredients, in a field wherein weeds are to be controlled;
   (b) applying a composition comprising one or more fungicidal active ingredients, in a field wherein harmful microorganisms are to be controlled; and/or
   (c) applying a composition comprising one or more insecticidal active ingredients, in a field wherein pests are to be controlled.

3. The method according to claim 2, wherein:
   (a) the one or more herbicidal active ingredients is amitrol, carfentrazone, clethodim, clopyralid, dicamba, diquat, ethalfluralin, ethametsulfuron-methyl, florasulam, imazamox, imazapyr, glufosinate, glufosinate-ammonium, glyphosate, MCPA amine, MCPA ester, metsulfuron, quizalofop-p-ethyl, quinclorac, saflufenacil, triallate, and/or trifluralin;
   (b) the one or more fungicidal active ingredients is azoxystrobin, benzovindiflupyr, boscalid, cyprodinil, fludioxonil, fluxapyroxad, fluopyram, ipfentrifluconazole, iprodione, isoflucypram, metalaxyl, mefenoxam, mefentrifluconazole, metconazole, penthiopyrad, picoxystrobin, propiconazole, prothioconazole, pyraclostrobin, pyraziflumid, pydiflumetofen, sedaxane, and/or tebuconazole; and/or
   (c) the one or more insecticidal active ingredients is broflanilide, carbaryl, carbofuran, chlorantraniliprole, chlorpyrifos, cypermethrin, cyclaniliprole, cyhalodiamide, clothianidin, deltametinin, dimethoate, cyantraniliprole, cyhalothrin-lambda, imidacloprid, lambda-cyhalothrin, permethrin, sulfoxaflor, spirotetramate, tetraniliprole, and/or thiamethoxam.

4. The method according to claim 3, wherein the one or more herbicidal active ingredients comprises glufosinate or glufosinate ammonium.

5. A method of producing an inbred plant, the method comprising selecting a plant and selfing the selected plant and its descendants for several generations to produce the inbred plant, wherein the selected plant is derived from the plant of claim 1.

6. The method of claim 5, further comprising doubling a haploid to produce a double haploid inbred plant, wherein the haploid is the selected plant or descendant thereof derived from the Canola plant of Canola hybrid variety 7CN0020.

7. A method of producing F2 seed, the method comprising selfing the Canola hybrid plant of claim 1, or breeding said plant with another plant to produce F1 seed, growing said F1 seed to produce F1 plants, and selfing or breeding said F1 plants to produce F2 seed.

8. A method of producing a clean seed, the method comprising obtaining the seed of Canola hybrid variety 7CN0020, wherein a representative sample of seed of that variety has been deposited under Accession Number NCIMB 43759, and cleaning said seed.

9. A treated seed of Canola hybrid variety 7CN0020, representative seed of said variety having been deposited under the Accession Number NCIMB 43759.

10. A method of producing the treated seed of claim 9, the method comprising obtaining the seed of Canola hybrid variety 7CN0020, wherein a representative sample of seed of that variety has been deposited under Accession Number NCIMB 43759, and treating said seed.

11. A method of producing a commodity product, the method comprising obtaining seed produced by an F1 hybrid Canola plant designated 7CN0020, seed of said hybrid having been deposited under Accession Number NCIMB 43759, and preparing the commodity product, wherein said commodity product comprises seed oil, meal, fiber or protein.

12. A method of producing a commercial crop, the method comprising planting the seed of Canola hybrid variety 7CN0020, wherein a representative sample of seed of that variety has been deposited under Accession Number NCIMB 43759, and growing the commercial crop.

* * * * *